US008124754B2

(12) United States Patent
Inoue et al.

(10) Patent No.: US 8,124,754 B2
(45) Date of Patent: Feb. 28, 2012

(54) DOUBLE-STRANDED NUCLEIC ACID MOLECULE CANCER CELL PROLIFERATION INHIBITOR AND PHARMACEUTICAL AGENT SUITABLE FOR PREVENTION OR TREATMENT OF UTERINE CANCER, BREAST CANCER, AND BLADDER CANCER

(75) Inventors: Satoshi Inoue, Saitama (JP); Kazuhiro Ikeda, Saitama (JP)

(73) Assignees: Saitama Medical University, Saitama (JP); RNAI Co., Ltd., Tokyo (JP)

( * ) Notice: Subject to any disclaimer, the term of this patent is extended or adjusted under 35 U.S.C. 154(b) by 9 days.

(21) Appl. No.: 12/642,979

(22) Filed: Dec. 21, 2009

(65) Prior Publication Data
US 2010/0173405 A1 Jul. 8, 2010

Related U.S. Application Data

(63) Continuation of application No. PCT/JP2008/061346, filed on Jun. 20, 2008.

(30) Foreign Application Priority Data

Jun. 20, 2007 (JP) .................................. 2007-162641

(51) Int. Cl.
C07H 21/02 (2006.01)
C07H 21/04 (2006.01)
C12N 15/11 (2006.01)

(52) U.S. Cl. ..................... 536/24.5; 536/23.1; 536/24.3; 536/24.33; 514/44

(58) Field of Classification Search ................. 536/23.1, 536/24.3, 24.33, 24.5
See application file for complete search history.

(56) References Cited

U.S. PATENT DOCUMENTS
2005/0153918 A1   7/2005   Chabot et al.
2007/0179160 A1   8/2007   Helleday

FOREIGN PATENT DOCUMENTS
| JP | 2006-500916 A | 1/2006 |
| JP | 3803318 B2 | 5/2006 |
| JP | 2006-528618 A | 12/2006 |
| WO | WO 03/102185 A2 | 12/2003 |
| WO | WO 2005/012524 A1 | 2/2005 |

OTHER PUBLICATIONS
Ueyama et al. (Cancer Gene Therapy, 2010 vol. 17, 624-632).*
International Search Report for PCT/JP2008/061346, mailed Aug. 12, 2008.

(Continued)

*Primary Examiner* — Terra Cotta Gibbs
(74) *Attorney, Agent, or Firm* — Buchanan Ingersoll & Rooney PC

(57) ABSTRACT

A double-stranded nucleic acid molecule for suppressing the expression of at least one of COX7RP and Efp genes which includes (a) a sense strand which includes a nucleotide sequence corresponding to a target sequence indicated by any one of SEQ ID Nos.: 1 to 38 and (b) an antisense strand which includes a nucleotide sequence complementary to that of the sense strand specified in (a); a cancer cell proliferation inhibitor with the double-stranded nucleic acid molecule and against at least one of uterine, breast and bladder cancer cells; and a pharmaceutical agent with the cancer cell proliferation inhibitor and against at least one of uterine, breast and bladder cancers.

11 Claims, 16 Drawing Sheets

OTHER PUBLICATIONS

Written Opinion of the International Searching Authority for PCT/JP2008/061346, mailed Aug. 12, 2008.
Response to Written Opinion for PCT/JP2008/061346.
Tomohiko Urano et al., "Efp targets 14-3-3σ for proteolysis and promotes breast tumour growth," Nature, 2002, pp. 871-875, vol. 417, Nature Publishing Group.
Weiguo Zou et al., "The Interferon-inducible Ubiquitin-protein Isopeptide Ligase (E3) EFP Also Functions as an ISG15 E3 Ligase," Journal of Biological Chemistry, Feb. 17, 2006, pp. 3989-3994, vol. 281, No. 7, The American Society for Biochemistry and Molecular Biology, Inc.
Toru Watanabe et al., "Isolation of Estrogen-Responsive Genes with a CpG Island Library," Molecular and Cellular Biology, Jan. 1998, pp. 442-449, vol. 18, No. 1, American Society for Microbiology.
Rutsuko Hobo-Hayashi "Expression and Regulation of an Estrogen-Responsive Gene, Cytochrome C Oxidase Subunit 7a Related Polypeptide (COX7RP) in Endometrial Cancer," J. Saitama Medical School, 2004, pp. 199-206, vol. 31.

* cited by examiner

Ishikawa cells

HeLa cells

Ishikawa cells

MCF7 cells

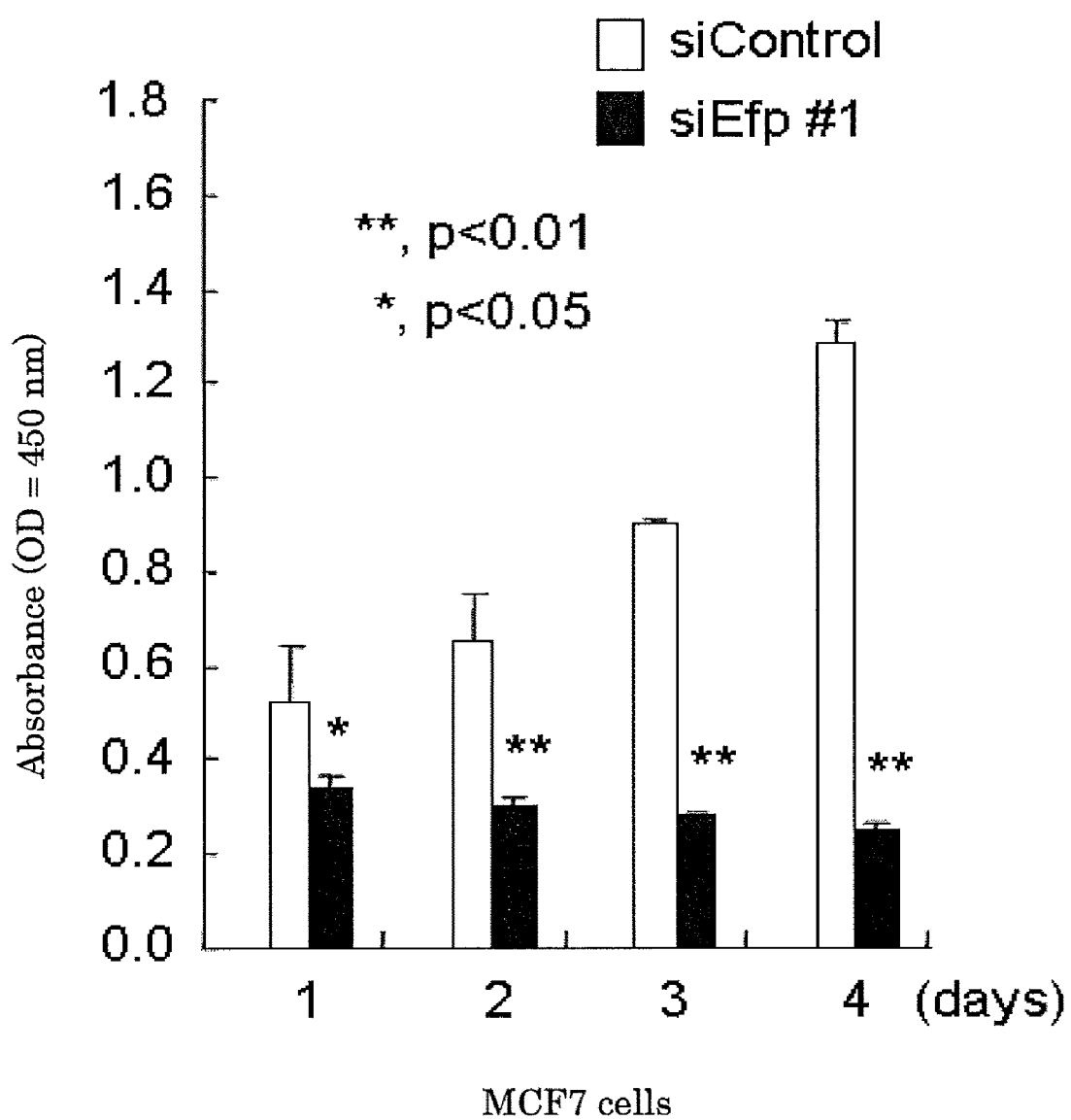

EJ cells

Ishikawa cells

MCF7 cells

Ishikawa cells

MCF7 cells

EJ cells

EJ cells

Ishikawa cells

Ishikawa cells

Ishikawa cells

Ishikawa cells

Ishikawa cells

Chimera  Chimera
siControl-Efp  siEfp #1

Ishikawa cells

Chimera                        Chimera
siControl-Efp    4.5 weeks     siEfp #1

DOUBLE-STRANDED NUCLEIC ACID MOLECULE CANCER CELL PROLIFERATION INHIBITOR AND PHARMACEUTICAL AGENT SUITABLE FOR PREVENTION OR TREATMENT OF UTERINE CANCER, BREAST CANCER, AND BLADDER CANCER

CROSS-REFERENCE TO RELATED APPLICATION

This is a continuation application of PCT/JP2008/061346, filed on Jun. 20, 2008.

TECHNICAL FIELD

The present invention relates to a double-stranded nucleic acid molecule (e.g., siRNA) suitable for the prevention or treatment of uterine, breast and bladder cancers; a cancer cell proliferation inhibitor containing the double-stranded nucleic acid molecule; and a pharmaceutical agent containing the cancer cell proliferation inhibitor.

BACKGROUND ART

Breast and uterine cancers are both known as hormone-dependent cancer, and estrogen—a sex steroid hormone—relates closely to the development and proliferation thereof. One conventional method for the treatment of breast cancer is an endocrine therapy using an anti-estrogen drug (tamoxifen) which binds to an estrogen receptor (ER) serving as a transcriptional factor to inhibit the transcriptional activity thereof. But, this method poses a problem in that relapse occurs as a result of acquisition of drug resistance in the course of the treatment. Also, this drug has been elucidated to increase the risk of the development of uterine cancer, and problematically has severe adverse side effects. Meanwhile, in one method for the treatment of uterine cancer, progestin—a synthetic drug similar to progesterone (hormone)—is administered to subjects to inhibit the effect of estrogen on the uterus. But, this method, problematically, makes their feelings unstable and increases their body weights, for example.

In order to overcome the above-described problems in such conventional treatment methods, there is a need to reveal the mechanism of estrogen action in breast and uterine cancers and explore a new molecular target on the basis of that mechanism.

Meanwhile, the bladder is an internal organ differentiated from the genitourinary system similar to the uterus and other organs and thus, presumably, is controlled by sex hormones such as estrogen and androgen. In addition, in menopausal disorders due to estrogen deficiency, bladder disorders are likely to occur. Although the relation between bladder cancer and sex hormones has not yet been elucidated, generally, bladder cancer is known to develop in male more than in female. As conventional method for the treatment of bladder cancer, surgical total cystectomy is often performed. After total cystectomy, however, urinary tract diversion is required for all the subjects. As a result, their lifestyles must be changed in some cases, leading to deterioration in quality of life (QOL). In recent years, therefore, a bladder conservation therapy is attempted depending on the cases of interest. But, there are many cases in which an anti-cancer agent, an irradiation therapy, etc. are not effective.

In order to overcome the above-described problems in such conventional treatment methods, demand has arisen for the development of a therapy for bladder cancer which is based on a different action mechanism from conventional cases and has adverse side effects to a less extent.

Meanwhile, in recent years, many attempts have been made to apply, to a cancer therapy, a technique of RNA interference (RNAi) which can suppress the expression of a target gene in a sequence-specific manner by introducing into cells a small-molecule RNA of about 18 to about 29 bases (short interfering RNA (siRNA)). Actually, many literatures report that the proliferation of cancer cells can be inhibited using siRNA targeting the gene involved in the cancer (for example, Japanese Patent Application Laid-Open (JP-A) Nos. 2006-500916 and 2006-528618). However, in order for such RNAi technique to be applied to actual medical treatments, there is a need to develop excellent siRNA which has a high expression suppressive effect on and a high specificity to a target gene. At present, further development is demanded.

DISCLOSURE OF INVENTION

The present invention solves the above existing problems and aims to achieve the following objects. Specifically, an object of the present invention is to provide a double-stranded nucleic acid molecule (e.g., siRNA) which can effectively inhibit the proliferation of uterine, breast and bladder cancer cells by suppressing the expression of at least one target gene of COX7RP and estrogen-responsive finger protein ("Efp") genes (estrogen-responsive genes). Another object of the present invention is to provide a cancer cell proliferation inhibitor containing the double-stranded nucleic acid molecule. Still another object of the present invention is to provide a pharmaceutical agent containing the cancer cell proliferation inhibitor.

The present inventors conducted extensive studies to solve the above-described problems, and as a result have obtained the following findings. Specifically, according to one finding, siRNA having a specific sequence and produced by the present inventors and chimera siRNA identical to the siRNA except that part of the RNA sequence thereof is changed to a DNA sequence have a remarkably excellent suppressive effect on the expressions of COX7RP and Efp genes (estrogen-responsive genes), and can effectively inhibit the proliferation of uterine, breast and bladder cancer cells by suppressing the expressions of these genes. Further, according to the other finding, such siRNA and chimera siRNA can be suitably used as an active ingredient of a pharmaceutical agent for the prevention or treatment of uterine, breast and bladder cancers.

COX7RP and Efp genes are both an estrogen-responsive gene whose expression is induced by estrogen, and are known to be overexpressed in uterine and breast cancers. The present inventors, this time, have newly found out siRNA and chimera siRNA which efficiently and specifically suppress the expressions of these genes. Also, the present inventors have found that, when injected into a cancer formed in a nude mouse tumor growth model into which the cells belonging to breast (MCF7 cells), uterine (Ishikawa cells) and bladder (EJ cells) cancer cell lines have subcutaneously been transplanted, these siRNA and chimera siRNA can remarkably inhibit the growth of each cancer (see Examples given below). These results indicate that COX7RP and Efp genes relates closely to the growth of uterine, breast and bladder cancers, and can become a new molecular target for these cancers. Notably, the expressions and functions of COX7RP and Efp genes in bladder cancer have not been elucidated so far. But, for the first time in the present invention, the expression of Efp gene in bladder cancer cells is confirmed, and this gene is elucidated to be involved in the growth of bladder cancer. The present invention shows a probability of the double-stranded nucleic acid molecule as a new therapeutic drug for the treatment of bladder cancer. The double-stranded nucleic acid molecule can be presumably applied to the treatment of bladder cancer with a less degree of adverse side effects on the basis of a different action mechanism from conventional cases.

Presumably, the siRNA and chimera siRNA produced by the present inventors can be suitably used as an active ingredient of a new pharmaceutical agent for the prevention or treatment of uterine, breast and bladder cancers. Furthermore, these siRNA and chimera siRNA unveil the mechanism of the proliferation of uterine, breast and bladder cancer cells, and are expected to help further elucidation of pathological conditions in these cancers.

The present invention has been accomplished on the basis of the findings obtained by the present inventors. Means for solving the above problems are as follows.

<1> A double-stranded nucleic acid molecule including:
(a) a sense strand which includes a nucleotide sequence corresponding to a target sequence indicated by any one of SEQ ID Nos.: 1 to 38, and
(b) an antisense strand which includes a nucleotide sequence complementary to that of the sense strand specified in (a),
wherein the double-stranded nucleic acid molecule is for suppressing the expression of at least one of COX7RP and Efp genes.

<2> The double-stranded nucleic acid molecule according to <1> above, wherein the sense strand has a nucleotide sequence which corresponds to a target sequence indicated by any one of SEQ ID Nos.: 1 to 5 and 16 to 21.

<3> The double-stranded nucleic acid molecule according to <2> above, wherein the sense strand has a nucleotide sequence which corresponds to a target sequence indicated by any one of SEQ ID Nos.: 1, 2, 4, 5, 16, 18, 19, 20 and 21.

<4> The double-stranded nucleic acid molecule according to <3> above, wherein the sense strand has a nucleotide sequence which corresponds to a target sequence indicated by any one of SEQ ID Nos.: 1, 2 and 16.

<5> The double-stranded nucleic acid molecule according to <4> above, wherein the sense strand has a nucleotide sequence which corresponds to a target sequence indicated by any one of SEQ ID Nos.: 2 and 16.

<6> The double-stranded nucleic acid molecule according to any one of <1> to <5> above, wherein the double-stranded nucleic acid molecule is at least one of a double-stranded RNA and a double-stranded RNA-DNA chimera.

<7> The double-stranded nucleic acid molecule according to <6> above, wherein the double-stranded nucleic acid molecule is at least one of siRNA and chimera siRNA.

<8> The double-stranded nucleic acid molecule according to <7> above, wherein the double-stranded nucleic acid molecule is chimera siRNA composed of a sense strand in which eight bases at the 3' side are DNA bases and the other bases are RNA bases, and an antisense strand in which six bases at the 5' side are DNA bases and the other bases are RNA bases.

<9> The double-stranded nucleic acid molecule according to any one of <1> to <8> above, wherein each of the sense and antisense strands has a structure with two to six overhanging bases at the 3' end.

<10> The double-stranded nucleic acid molecule according to any one of <1> to <9> above, wherein the double-stranded nucleic acid molecule is modified.

<11> DNA including:
a nucleotide sequence which encodes the double-stranded nucleic acid molecule according to any one of <1> to <10> above.

<12> A vector including:
the DNA according to <11> above.

<13> The vector according to <12> above, wherein the vector is any one of a plasmid vector and a virus vector.

<14> The vector according to any one of <12> and <13> above, wherein the vector is a tandem-type siRNA expression vector.

<15> The vector according to any one of <12> and <13> above, the vector is a hairpin-type siRNA expression vector.

<16> A cancer cell proliferation inhibitor including:
at least one of the double-stranded nucleic acid molecule according to any one of <1> to <10> above, the DNA according to <11> above, and the vector according to any one of <12> to <15> above,
wherein the cancer cell proliferation inhibitor is for inhibiting the growth of at least one of uterine cancer cells, breast cancer cells and bladder cancer cells.

<17> A method for inhibiting the proliferation of at least one of uterine cancer cells, breast cancer cells and bladder cancer cells, the method including:
making at least one of the double-stranded nucleic acid molecule according to any one of <1> to <10> above, the DNA according to <11> above, and the vector according to any one of <12> to <15> above act on at least one of uterine cancer cells, breast cancer cells, and bladder cancer cells.

<18> A pharmaceutical agent including:
the cancer cell proliferation inhibitor according to <16> above,
wherein the pharmaceutical agent is for preventing or treating at least one of uterine cancer, breast cancer and bladder cancer.

<19> A method for preventing or treating at least one of uterine, breast and bladder cancers, the method including:
administering to an individual the cancer cell proliferation inhibitor according to <16> above.

The present invention can provide a double-stranded nucleic acid molecule (e.g., siRNA) which can effectively inhibit the proliferation of uterine, breast and bladder cancer cells by suppressing the expression of at least one target gene of COX7RP and Efp genes (estrogen-responsive genes); a cancer cell proliferation inhibitor containing the double-stranded nucleic acid molecule; and a pharmaceutical agent containing the cancer cell proliferation inhibitor. These can solve the existing problems.

BRIEF DESCRIPTION OF DRAWINGS

FIG. 7B is a graph which shows the inhibitory effect of siEfp#1 on the proliferation of MCF7 cells.

Figure 1A:
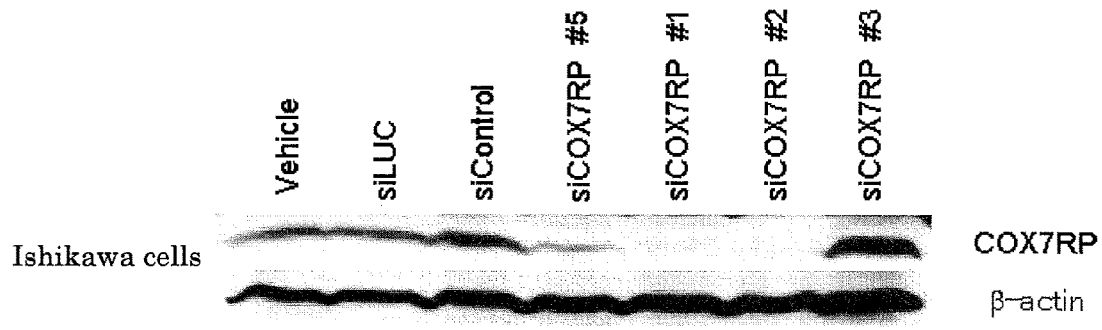
FIG. 1A is a western blot image which shows the suppressive effect of each siCOX7RP on the expression of COX7RP in Ishikawa cells.

BEST MODE FOR CARRYING OUT THE INVENTION (Double-Stranded Nucleic Acid Molecule)

A double-stranded nucleic acid molecule of the present invention suppresses the expression of at least one of COX7RP and Efp genes, and is characterized in that it contains (a) a sense strand which includes a nucleotide sequence corresponding to a target sequence indicated by any one of SEQ ID Nos.: 1 to 38 and (b) an antisense strand which includes a nucleotide sequence complementary to that of the sense strand specified in (a).

Notably, in the present invention, the term "double-stranded nucleic acid molecule" refers to a double-stranded nucleic acid molecule in which a desired sense strand is hybridized with an antisense strand complementary thereto.
<COX7RP and Efp Genes>

As described above, each of COX7RP and Efp genes is an estrogen-responsive gene whose expression is induced by estrogen, and is known to be overexpressed in uterine and breast cancers. Notably, in bladder cancer, the expression or function of COX7RP and Efp genes has not been elucidated so far.

In the present invention, the double-stranded nucleic acid molecule targets the mRNA sequence of COX7RP or Efp gene and suppresses the expression thereof. As used herein, COX7RP or Efp gene may be referred to as a "target gene" of the double-stranded nucleic acid molecule.

Notably, for reference, the nucleotide sequence of human COX7RP gene is shown as SEQ ID No.: 41, and that of human Efp gene is shown as SEQ ID No.: 42.
<Sense and Antisense Strands>

As described above, the present inventors conducted extensive studies and have found that the expression of COX7RP or Efp gene is remarkably suppressed by the double-stranded nucleic acid molecule that contains an antisense strand having a nucleotide sequence complementary to, among others, a certain target sequence (any one of SEQ ID Nos.: 1 to 38) and corresponding to part of the mRNA sequence of COX7RP or Efp gene. Thus, the double-stranded nucleic acid molecule of the present invention contains (a) a sense strand which includes a nucleotide sequence corresponding to a target sequence indicated by any one of SEQ ID Nos.: 1 to 38 and (b) an antisense strand which includes a nucleotide sequence complementary to that of the sense strand specified in (a).

Here, the sense and antisense strands may be an RNA strand or an RNA-DNA chimera strand. The sense and antisense strands are hybridized with each other to form the double-stranded nucleic acid molecule.

Notably, among the sequences indicated by SEQ ID Nos.: 1 to 38, those indicated by SEQ ID Nos.: 1 to 15 are derived from the sequence of human COX7RP gene (SEQ ID No.: 41), and those indicated by SEQ ID Nos.: 16 to 38 are derived from the sequence of human Efp gene (SEQ ID No.: 42).

In particular, the double-stranded nucleic acid molecule preferably has a sense strand which includes a nucleotide sequence corresponding to a target sequence indicated by any one of SEQ ID Nos.: 1 to 5 and 16 to 21; more preferably has a sense strand which includes a nucleotide sequence corresponding to a target sequence indicated by any one of SEQ ID Nos.: 1, 2, 4, 5, 16, 18, 19, 20 and 21; still more preferably has a sense strand which includes a nucleotide sequence corresponding to a target sequence indicated by any one of SEQ ID Nos.: 1, 2 and 16; particularly preferably has a sense strand which includes a nucleotide sequence corresponding to a target sequence indicated by any one of SEQ ID Nos.: 2 and 16.

When the sense strand is that other than the sense strands given above as a preferred sense strand, there may be the case where the expression suppressive effect of the double-stranded nucleic acid molecule on the target gene becomes weak. In contrast, in the case where the sense strand is that given above as a particularly preferred sense strand, it is advantageous in that, even when the double-stranded nucleic acid molecule is used in a small amount, the expression suppressive effect on the target gene becomes strong.

<Type>

The type of the double-stranded nucleic acid molecule is not particularly limited and may be appropriately selected depending on the purpose. Examples thereof include double-stranded RNAs (dsRNAs) and double-stranded RNA-DNA chimeras.

Here, the term "double-stranded RNA" refers to a double-stranded nucleic acid molecule whose sense and antisense strands are both an RNA sequence. The term "double-stranded RNA-DNA chimera" refers to a double-stranded nucleic acid molecule whose sense and antisense strands are both an RNA-DNA chimera sequence.

The double-stranded RNA is particularly preferably small interfering RNA (siRNA). Here, siRNA is small-molecule double-stranded RNA with a base length of 18 to 29, and has the function of cleaving mRNA of a target gene with a sequence complementary to the antisense strand (guide strand) of the siRNA and suppressing the expression of the target gene.

The end structure of the siRNA is not particularly limited, so long as the siRNA has the above-described sense and antisense strands and can suppress the expression of the target gene, and may be appropriately selected depending on the purpose. For example, the siRNA may have a blunt end or a cohesive end (overhang). In particular, each strand of the siRNA preferably has an end structure with two to six overhanging bases at its 3' end, more preferably has an end structure with two overhanging bases at its 3' end.

Also, the double-stranded RNA may be short hairpin RNA (shRNA). Here, the shRNA is single-stranded RNA which contains a dsRNA region of about 18 to about 29 bases and a loop region of about three to about nine bases. After expression in vivo, base pairs are formed to become hairpin-shaped double-stranded RNA (shRNA). Thereafter, the shRNA is cleaved by Dicer (RNase III enzyme) to be siRNA, and the thus-formed siRNA can suppress the expression of a target gene.

Similar to siRNA, the end structure of the shRNA is not particularly limited and may be appropriately selected depending on the purpose. For example, the shRNA may have a blunt end or a cohesive end (overhang).

Meanwhile, the double-stranded RNA-DNA chimera is particularly preferably chimera siRNA. Here, the chimera siRNA is an 18- to 29-base small-molecule double-stranded RNA-DNA chimera which is identical to the original siRNA except that part of the RNA sequence is changed to a DNA sequence. In particular, preferred is a 21- to 23-base small-molecule double-stranded RNA-DNA chimera which is formed by changing, to DNA bases, eight bases at the 3' side of the original siRNA's sense strand and six bases at the 5' side of the original siRNA's antisense strand. Similar to siRNA, the chimera siRNA has the function of suppressing the expression of a target gene.

Similar to siRNA, the end structure of the chimera siRNA is not particularly limited and may be appropriately selected depending on the purpose. For example, the chimera siRNA may have a blunt end or a cohesive end (overhang).

The chimera siRNA (double-stranded RNA-DNA chimera) is advantageous, for example, in that it is highly stable in blood, involves low immune response induction, and is produced at low cost.

<Modification>

Also, the double-stranded nucleic acid molecule may be appropriately modified depending on the purpose. The double-stranded nucleic acid molecule may be subjected to 2'O-methylation, phosphorothioate modification (S-modification), Locked Nucleic Acid (LNA) modification, etc., in order for the double-stranded nucleic acid molecule to have, for example, resistance to a nucleolytic enzyme (nuclease) and improved stability in culture or in vivo. Further, for example, in order for the double-stranded nucleic acid molecule to be increased in transfection efficiency into cells, the 5' or 3' end of the sense strand of the double-stranded nucleic acid molecule may be modified with, for example, nanoparticles, cholesterol, or a peptide allowing it to pass through a cell membrane.

Notably, such modification of the double-stranded nucleic acid molecule may be appropriately performed by a conventionally known method without any restriction.

<Production Method>

The production method for the double-stranded nucleic acid molecule is not particularly limited and may be a conventionally known production method.

For example, the siRNA can be produced as follows. Specifically, 18- to 29-base single-stranded RNA fragments, each serving as a desired sense strand and an antisense strand complementary thereto, are chemically synthesized using, for example, an existing DNA/RNA auto-synthesizer; and then the thus-synthesized fragments are annealed. Also, an annealed double-stranded siRNA is commercially available. Furthermore, one can request the synthesis of the siRNA to siRNA-synthesizing companies. Moreover, when a desired siRNA expression vector like the below-described vector of the present invention is constructed and introduced into cells, the siRNA can be produced utilizing intracellular reactions.

Meanwhile, the chimera siRNA can be produced, for example, as follows. Specifically, sense and antisense strands each of which is a chimera nucleic acid molecule are chemically synthesized; and the thus-synthesized strands are annealed (see, for example, Japanese Patent (JP-B) No. 3803318).

(DNA and Vector)

DNA of the present invention contains a nucleotide sequence which encodes the double-stranded nucleic acid molecule of the present invention. Also, a vector of the present invention contains the above DNA.

<DNA>

The DNA is not particularly limited, so long as it contains a nucleotide sequence encoding the above-described double-stranded nucleic acid molecule of the present invention, and may be appropriately selected depending on the purpose. In particular, a promoter sequence, which is for controlling the transcription of the double-stranded nucleic acid molecule, is preferably linked upstream (5' side) of the nucleotide sequence encoding it. The promoter sequence is not particularly limited and may be appropriately selected depending on the purpose. Examples thereof include pol II promoters (e.g., a CMV promoter) and pol III promoters (e.g., an H1 promoter and a U6 promoter). In addition, a terminator sequence, which is for terminating the transcription of the double-stranded nucleic acid molecule, is preferably linked downstream (3' side) of the nucleotide sequence encoding it. Similarly, the terminator sequence is not particularly limited and may be appropriately selected depending on the purpose. One preferred embodiment of the DNA is a transcriptional unit containing a promoter sequence, a nucleotide sequence encoding the double-stranded nucleic acid molecule, and a terminator sequence. Notably, the transcriptional unit can be constructed by a conventionally known method.

<Vector>

The vector is not particularly limited, so long as it contains the DNA, and may be appropriately selected depending on the purpose. Examples of the type thereof include a plasmid vector and a virus vector. Also, the vector is preferably an expression vector capable of expressing the double-stranded nucleic acid molecule. The manner in which the double-stranded nucleic acid molecule is expressed is not particularly limited. Examples of the method for expressing the siRNA include a method in which two short single-stranded RNAs are expressed in a tandem manner (tandem type) and a method in which one single-stranded RNA is expressed as shRNA (hairpin type).

The tandem-type siRNA expression vector has DNA which contains a DNA sequence encoding the siRNA's sense strand and that encoding the siRNA's antisense strand, each of the DNA sequences having a promoter sequence linked upstream (5' side) thereof and a terminator sequence linked downstream (3' side) thereof.

The hairpin-type siRNA expression vector has DNA which contains a DNA sequence encoding the siRNA's sense strand and that encoding the siRNA's antisense strand, wherein the sense strand's DNA sequence and the antisense strand's DNA sequence are disposed in an opposite direction to each other and linked via a loop sequence to each other. Here, each of the DNA sequences has a promoter sequence linked upstream (5' side) thereof and a terminator sequence linked downstream (3' side) thereof.

The above vectors can be constructed by a conventionally known method. For example, a vector is cut in advance with a restriction enzyme, and then the DNA is ligated to the cut sites thereof.

When the DNA or vector is introduced (transfected) into cells, the promoters are activated, whereby the double-stranded nucleic acid molecule can be produced. For example, in the case of the tandem-type vector, the DNA is transcribed in cells to form sense and antisense strands, which are then hybridized with each other to produce siRNA. In the case of the hairpin-type vector, the DNA is transcribed in cells to form hairpin-type RNA (shRNA), which then undergoes processing by a dicer to produce siRNA.

(Cancer Cell Proliferation Inhibitor)

A cancer cell proliferation inhibitor of the present invention is a cancer cell proliferation inhibitor (tumor growth inhibitor) which suppresses the proliferation of at least one of uterine, breast and bladder cancer cells. The cancer cell proliferation inhibitor contains at least one of the double-stranded nucleic acid molecule, the DNA and the vector of the present invention; and, if necessary, further contains other ingredients.

<Double-Stranded Nucleic Acid Molecule, DNA and Vector>

The double-stranded nucleic acid molecule is previously described in detail in relation to that of the present invention. The double-stranded nucleic acid molecule can effectively suppress the expression of at least one of target COX7RP and Efp genes and thus, is suitably used as an active ingredient of the cancer cell proliferation inhibitor which is for suppressing the proliferation of at least one of uterine, breast and bladder cancer cells. Similarly, the DNA and the vector are previously described in detail in relation to those of the present invention.

The amount of at least one of the double-stranded nucleic acid molecule, the DNA or the vector contained in the cancer cell proliferation inhibitor is not particularly limited and may be appropriately determined depending on the purpose. Also, the cancer cell proliferation inhibitor may be at least one of the double-stranded nucleic acid molecule itself, the DNA itself or the vector itself.

<Other Ingredients>

The other ingredients are not particularly limited and may be appropriately selected depending on the purpose. Examples thereof include diluents (e.g., physiological saline and culture) which dilute at least one of the double-stranded nucleic acid molecule, the DNA and the vector to a desired concentration; and transfection reagents which are for introducing (transfecting) at least one of the double-stranded nucleic acid molecule, the DNA and the vector into cells of interest.

The amount of the other ingredients contained in the cancer cell proliferation inhibitor is not particularly limited and may be appropriately determined depending on the purpose.

<Uterine, Breast and Bladder Cancer Cells>

The cells to which the cancer cell proliferation inhibitor is applied are at least one of uterine, breast and bladder cancer cells. These cancer cells may be those cultured in vitro or those present in a patient suffering from uterine cancer, breast cancer and/or bladder cancer. The uterine, breast and bladder cancer cells which are cultured in vitro are not particularly limited and may be appropriately selected depending on the purpose. Examples of the uterine cancer cells include Ishikawa cells (derived from human endometrial cancer) and HeLa cells (derived from human cervical cancer). Examples of the breast cancer cells include MCF7 cells (derived from human breast cancer). Examples of the bladder cancer cells include EJ cells (derived from human bladder cancer). These cells are available from American Type Culture Collection (ATCC) or JCRB Cell Bank.

<Effects>

When introduced (transfected) into, for example, at least one of uterine, breast and bladder cancer cells, the cancer cell proliferation inhibitor can act on these cells. The method for introducing it into the cells is not particularly limited and may be appropriately selected from conventionally known methods depending on the purpose. Examples thereof include a method using transfection reagents, a method based on electroporation, a method using magnetic particles and a method utilizing viral infection.

The amount of the cancer cell proliferation inhibitor which acts on at least one of uterine, breast and bladder cancer cells is not particularly limited and may be appropriately determined in consideration of, for example, the type of cell and the intended degree of the effects. For example, the amount is preferably about 0.1 µg (as reduced to the amount of an active ingredient (double-stranded nucleic acid molecule)), more preferably about 5 µg, particularly preferably about 15 µg, with respect to $1 \times 10^6$ cells.

<Cancer Cell Proliferation Inhibiting Method>

The cancer cell proliferation inhibitor contains at least one of the double-stranded nucleic acid molecule, the DNA and the vector and thus, acts on at least one of uterine, breast and bladder cancer cells; i.e., suppresses the expression of at least one of COX7RP and Efp genes, to thereby effectively suppress the proliferation of uterine, breast and bladder cancer cells. The present invention, therefore, also relates to a method for inhibiting the proliferation of cancer cells (tumor growth inhibiting method) which is characterized in that at least one of the double-stranded nucleic acid molecule, the DNA and the vector is made to act on at least one of uterine, breast and bladder cancer cells.

(Pharmaceutical Agent)

A pharmaceutical agent of the present invention prevents or treats at least one of uterine, breast and bladder cancers. The pharmaceutical agent contains the above-described cancer cell proliferation inhibitor of the present invention; and, if necessary, further contains other ingredients.

<Cancer Cell Proliferation Inhibitor>

The cancer cell proliferation inhibitor is previously described in detail in relation to that of the present invention. The cancer cell proliferation inhibitor contains at least one of the double-stranded nucleic acid molecule, the DNA and the vector of the present invention and thus, can effectively suppress the proliferation of at least one of uterine, breast and bladder cancer cells by suppressing the expression of at least one of COX7RP and Efp genes. That is, the cancer cell proliferation inhibitor can be suitably used for the pharmaceutical agent which is for preventing or treating at least one of uterine, breast and bladder cancers.

The amount of the cancer cell proliferation inhibitor contained in the pharmaceutical agent is not particularly limited and may be appropriately determined depending on the purpose. The pharmaceutical agent may be the cancer cell proliferation inhibitor itself.

Here, the double-stranded nucleic acid molecule serving as an active ingredient of the pharmaceutical agent may be the double-stranded nucleic acid molecule itself which has undergone no modification. In order to suitably attain intended preventive and/or therapeutic effects, the double-stranded nucleic acid molecule is preferably treated before use so as to have a form suitable for administration to a living subject.

For example, the double-stranded nucleic acid molecule is preferably modified from the viewpoint of improving stability of the double-stranded nucleic acid molecule in vivo. The modification applicable to the double-stranded nucleic acid molecule is not particularly limited. Examples thereof include 2'O-methylation, phosphorothioate modification (S-modification) and Locked Nucleic Acid (LNA) modification. Further, for example, in order for the double-stranded nucleic acid molecule to be increased in transfection efficiency into cells, the 5' or 3' end of the sense strand of the double-stranded nucleic acid molecule may be modified with, for example, nanoparticles, cholesterol, or a peptide allowing it to pass through a cell membrane. Such modification of the double-stranded nucleic acid molecule may be appropriately performed by a conventionally known method without any restriction.

Moreover, in view that the double-stranded nucleic acid molecule can be increased in transfection efficiency into cells, the double-stranded nucleic acid molecule preferably forms a complex together with liposome, polymer matrix, etc. The method for forming the complex is not particularly limited and may be appropriately selected from conventionally known methods.

<Other Ingredients>

The other ingredients are not particularly limited and may be appropriately selected depending on the purpose. Examples thereof include pharmaceutically acceptable carriers. The carriers are not particularly limited and may be appropriately selected depending on, for example, the dosage form thereof. Also, the amount of the other ingredients contained in the pharmaceutical agent is not particularly limited and may be appropriately determined depending on the purpose.

<Dosage Form>

The dosage form of the pharmaceutical agent is not particularly limited and may be appropriately selected depending on, for example, the below-described desired administration method. Examples thereof include oral solid preparations (e.g., tablets, coated tablets, granules, powder and capsules), oral liquid preparations (e.g., internal liquid preparations, syrups and elixirs), injections (e.g., solutions, suspensions and solid preparations to be reconstituted upon use), ointments, patches, gel, cream, external powder, spraying agents and inhalation powder.

The oral solid preparations can be produced through a routine method including adding to the active ingredient an excipient and other optionally used additives such as an integrating agent, a disintegrating agent, a lubricating agent, a coloring agent and a flavoring agent.

Examples of the excipient include lactose, sucrose, sodium chloride, glucose, starch, calcium carbonate, kaolin, microcrystalline cellulose and silicic acid. Examples of the integrating agent include water, ethanol, prop anol, simple syrup, glucose liquid, starch liquid, gelatin liquid, carboxymethyl cellulose, hydroxypropyl cellulose, hydroxypropyl starch, methyl cellulose, ethyl cellulose, shellac, calcium phosphate and polyvinylpyrrolidone. Examples of the disintegrating agent include dry starch, sodium alginate, agar powder, sodium hydrogen carbonate, calcium carbonate, sodium lauryl sulfate, monoglyceride stearate and lactose. Examples of the lubricating agent include purified talc, stearic acid salts, borax and polyethylene glycol. Examples of the coloring agent include titanium oxide and iron oxide. Examples of the flavoring agent include sucrose, bitter orange peel, citric acid and tartaric acid.

The oral liquid preparations can be produced through a routine method including adding to the active ingredient additives such as a flavoring agent, a buffer and a stabilizer.

Examples of the flavoring agent include sucrose, bitter orange peel, citric acid and tartaric acid. Examples of the buffer include sodium citrate. Examples of the stabilizing agent include tragacanth, gum arabic and gelatin.

The injections can be produced for use in subcutaneous, intramuscular and intravenous administrations through a routine method including adding to the anti-tumor agent additives such as a pH adjuster, a buffer, a stabilizer, a tonicity agent and a topical anesthetic.

Examples of the pH adjuster and buffer include sodium citrate, sodium acetate and sodium phosphate. Examples of the stabilizer include sodium pyrosulfite, EDTA, thioglycolic acid and thiolactic acid. Examples of the tonicity agent include sodium chloride and glucose. Examples of the topical anesthetic include procaine hydrochloride and lidocaine hydrochloride.

The ointment can be produced through a routine method including adding/mixing to/with the active ingredient a known base, stabilizing agent, moistening agent, preservative, etc.

Examples of the base include liquid paraffin, white petrolatum, bleached beeswax, octyldodecyl alcohol and paraffin.

Examples of the preservative include methyl parahydroxybenzoate, ethyl parahydroxybenzoate and propyl parahydroxybenzoate.

The patch can be produced through a routine method including applying onto a known support the ointment in the form of cream, gel, paste, etc. Examples of the support include woven or non-woven fabric made of cotton, staple fiber and chemical fiber; and films and foam sheets of soft vinyl chloride, polyethylene and polyurethane.

<Administration>

The pharmaceutical agent is suitable for the prevention or treatment of at least one of uterine, breast and bladder cancers. Notably, the uterine cancer encompasses both endometrial cancer (corpus uteri cancer, cancer of uterine body) and cervical cancer (cancer of cervix). Thus, in use, the pharmaceutical agent is preferably administered to a patient suffering from at least one of uterine, breast and bladder cancers.

The animal to which the pharmaceutical agent is administered is not particularly limited and may be appropriately selected depending on the purpose. Examples thereof include human, mouse, rat, bovine, pig, monkey, dog and cat, with human being particularly preferred.

The administration method for the pharmaceutical agent is not particularly limited and may be selected from topical and systemic administrations in consideration of, for example, the dosage form of the pharmaceutical agent, the type of disease and the conditions of a patient. When the topical administration is selected, the active ingredient (double-stranded nucleic acid molecule) of the pharmaceutical agent may be injected (administered) directly into a desired site (e.g., a tumor site), for example. The injection can be performed appropriately using conventionally known techniques (e.g., an injection). When the systemic administration (e.g., oral and intraperitoneal administrations, and administration to blood) is selected, preferably, a conventionally known drug delivery technique is appropriately used so that the active ingredient (double-stranded nucleic acid molecule) of the pharmaceutical agent can be stably and efficiently delivered to a desired site (e.g., a tumor site).

The dosage amount of the pharmaceutical agent is not particularly limited and may be appropriately determined depending on, for example, the age and body weight of a patient to which it is to be administered and the intended degree of the effects. For example, the dosage amount is preferably 1 mg to 100 mg as a daily dose for an adult, which are values reduced to the amount of the active ingredient (double-stranded nucleic acid molecule).

The number of doses of the pharmaceutical agent is not particularly limited and may be appropriately determined depending on, for example, the age and body weight of a patient to which it is to be administered and the intended degree of the effects.

The timing at which the pharmaceutical agent is administered is not particularly limited and may be determined depending on the purpose. For example, it may be administered for preventive or therapeutic purposes against the disease. In particular, the pharmaceutical agent inhibits the proliferation of uterine, breast and bladder cancer cells to effectively prevent tumor growth caused by the proliferation of these cancer cells. Thus, presumably, the pharmaceutical agent is desirably administered at an as early stage of the disease as possible.

<Prevention/Treatment Method>

The pharmaceutical agent contains the cancer cell proliferation inhibitor. Thus, when administered to an individual suffering from at least one of uterine, breast and bladder cancers, the pharmaceutical agent effectively inhibits the proliferation of uterine, breast and bladder cancer cells by suppressing the expression of at least one of COX7RP and Efp genes. As a result, at least one of uterine, breast and bladder cancers can be prevented or treated. The present invention, therefore, also relates to a prevention or treatment method for at least one of uterine, breast and bladder cancers, which is characterized in that the cancer cell proliferation inhibitor is administered to an individual.

EXAMPLES

The present invention will next be described by way of Examples, which should not be construed as limiting the present invention thereto.

Example 1

Production of Double-Stranded Nucleic Acid Molecule (siRNA))

As described below, there was provided a double-stranded nucleic acid molecule (siRNA) of the present invention and for suppressing the expression of at least one of COX7RP and Efp genes.

Specifically, each of siRNAs (siCOX7RPs) #1 to #4 targeting COX7RP gene and siRNAs (siEfps) #1 to #5 targeting Efp gene was synthesized in the form of double-stranded RNA. The double-stranded RNA was produced from the below-given gene sequence targeted by each siRNA and a sequence complementary thereto so that the double-stranded RNA had two overhanging bases at the 3' ends (RNAi Co., Ltd.). Also, siCOX7RP#5 was a double-stranded RNA synthesized from its targeting gene sequence (given below) and a sequence complementary thereto so that the double-stranded RNA had two overhanging DNA bases at the 3' ends (Dharmacon Inc.). Also, siEfp#6 was a double-stranded RNA composed of its targeting gene sequence (given below) and a sequence complementary thereto, having two overhanging uracil bases at the 3' ends, and obtained from siGENOME (trademark) SMARTpool (product of Dharmacon Inc.).

As a control, Luciferase GL2 Duplex (siLUC) (produced by Dharmacon Inc.) and siControl (produced by RNAi Co., Ltd.) were used.

The gene sequence targeted by each siRNA and its SEQ ID No. are shown below:

```
siCOX7RP#1:
5'-ctccgattccacagtgtatga-3',   (SEQ ID No.: 1)

siCOX7RP#2:
5'-gtgggagggaccatctactgc-3',   (SEQ ID No.: 2)

siCOX7RP#3:
5'-gctgaacacaggcttgttaat-3',   (SEQ ID No.: 3)

siCOX7RP#4:
5'-gtggcttcacgcagaagttgg-3',   (SEQ ID No.: 4)

siCOX7RP#5:
5'-ctgacctccgattccacagtg-3',   (SEQ ID No.: 5)

siEfp#1:
5'-gggtgggcgtgcttctcaact-3',   (SEQ ID No.: 16)

siEfp#2:
5'-gtccacctgatgtataagttc-3',   (SEQ ID No.: 17)

siEfp#3:
5'-gggatgagttcgagtttctgg-3',   (SEQ ID No.: 18)
```

-continued

```
siEfp#4:
5'-cggtgtcatctcctaacaagg-3',     (SEQ ID No.: 19)

siEfp#5:
5'-gcccgattcctcttagagaaa-3',     (SEQ ID No.: 20)

siEfp#6:
5'-gaccgcagctgcacaagaa-3',       (SEQ ID No.: 21)

siLUC:
5'-cgtacgcggaatacttcga-3'        (SEQ ID No.: 39)
and siControl:
5'-guaccgcacgucauucguauc-3'.     (SEQ ID No.: 40)
```

Example 2

Production of Double-Stranded Nucleic Acid Molecule (Chimera siRNA)

As described below, there was provided a double-stranded nucleic acid molecule (chimera siRNA) of the present invention and for suppressing the expression of at least one of COX7RP and Efp genes.

Chimera siRNA (chimera siCOX7RP#2) targeting COX7RP gene was produced using a base sequence which was identical to siCOX7RP#2, except that some bases were substituted with DNA bases. Similarly, chimera siRNA (chimera siEfp#1) targeting Efp gene was produced using a base sequence which was identical to siEfp#1, except that some bases were substituted with DNA bases. Specifically, in each chimera siRNA, eight RNA bases from the 3' end of the sense strand were substituted with DNA bases, and six RNA bases from the 5' end of the antisense strand were substituted with DNA bases.

Also, chimera siRNA (chimera siControl-COX7RP) serving as a negative control for chimera siCOX7RP#2 was produced through randomly rearranging the sequence of chimera siCOX7RP#2 and further substituting some bases with DNA bases. Also, chimera siRNA (chimera siControl-Efp) serving as a negative control for chimera siEfp#1 was produced through randomly rearranging the sequence of chimera siEfp#1 and further substituting some bases with DNA bases.

Notably, these chimera siRNAs were all produced by RNAi Co., Ltd.

The sense strand sequence of each chimera siRNA and its SEQ ID No. are shown below:

```
chimera siCOX7RP#2:
                                 (SEQ ID No.: 43)
5'-rGUrGrGrArGrGrGrArCrCrATCTACTGC-3', chimera siEfp#1:
                                 (SEQ ID No.: 44)
5'-rGrGrGUrGrGrGrCrGUrGrCUTCTCAACT-3', chimera siControl-COX7RP:
                                 (SEQ ID No.: 45)
5'-CTTrGUrGrGrArGrGrGrArCrArCATCGC-3'
and chimera siControl-Efp:
                                 (SEQ ID No.: 46)
5'-CTArGrGrGUrGrGrGrCrGUUrCrGTACCT-3'.
```

(Note that U, rG, rC and rA correspond to RNA bases; and T, G, C and A correspond to DNA bases.)

Example 3

Study on the Expression Suppressive Effect of siRNA and Chimera siRNA on Target Gene In Vitro Each of the siRNAs obtained in Example 1 and the chimera siRNAs obtained in Example 2 was transfected into culture cells derived from human uterine, breast and bladder cancers (Ishikawa cells, HeLa cells, MCF7 cells and EJ cells). Forty eight hours after, a protein sample was recovered and analyzed through western blotting, to thereby study the suppressive effect (knockdown effect) of the siRNA and chimera siRNA on the expression of COX7RP and Efp genes in the culture cells. The detail description of the experimental method is given below.

[Cell Culture]

Human endometrial cancer-derived Ishikawa cells 3H12 No. 74 were kindly provided by Dr. Masato Nishida of National Kasumigaura Hospital. Human cervical cancer-derived HeLa cells and human breast cancer-derived MCF7 cells were obtained from American Type Culture Collection. Human bladder cancer-derived EJ cells were obtained from JCRB Cell Bank. These cells were cultured in 5% $CO_2$ at 37° C. using Dulbaco's modified Eagle's medium (DMEM) (Sigma) containing 10% fetal calf serum (Roche), 100 units/mL penicillin (Invitrogen) and 100 μg/mL streptmysin (Invitrogen).

[Transfection]

On the day before transfection, the cultured cells were placed in a 6-well plate at a cell density of $5 \times 10^5$/well. Subsequently, Opti-MEM (Gibco) (250 μL/well) and Lipofectamine 2000 (Invitrogen) (10 μL/well) was mixed with each other, followed by incubating for 5 min at 37° C. The resultant mixture was added to a mixture of Opti-MEM (250 μL/well) and each siRNA (final concentration: 150 nM) or each chimera siRNA (final concentration: 150 nM), followed by further incubating at 37° C. for 20 min. The resultant mixture was added to the wells. Notably, in the case of EJ cells, siEfp#2 was used at a final concentration of 50 nM. The sample containing no siRNA was used as a solvent control (Vehicle).

Forty eight hours after the addition of the siRNA or chimera siRNA, the cells were recovered using 4× Sample Buffer (100 mM Tris-HCl, pH 6.5, 20% Glycerol, 4% SDS and 4% 2-Mercaptoethanol), followed by boiling at 100° C. for 15 min. Each sample was measured for OD 280 nm, and the obtained value was used to calculate the protein concentration on the basis of the calibration curve of BSA.

[Western Blot Analysis]

After 1,000 μg of the protein sample had been electrophoresed on an SDS-PAGE gel, the separated protein samples were blotted to Immobilon-P (Millipore). The protein was detected with ECL detection system (Amersham Pharmacia Biotech) using, as a primary antibody, an anti-Efp or COX7RP antibody (see Proceedings of the National Academy of Sciences of the United States of America., Vol. 90, No. 23, pp. 11,117-11,121, 1993 and Journal of Saitama Medical University 2004, Vol. 31, No. 4, pp. 199-206) and, as a secondary antibody, horseradish peroxidase (HRP)-conjugated anti-rabbit IgG antibody (Amersham Biosciences). After removal of the antibodies using Stripping Buffer (62.5 mM Tris-HCl, pH 6.7, 2% SDS and 100 mM 2-Mercaptoethanol), the detection was performed using, as a loading control, a primary antibody β-actin (SIGMA) and a secondary antibody HRP-conjugated anti-mouse IgG (Amersham Biosciences).

The results of Example 3 are shown in FIGS. 1A to 1C, FIGS. 2A and 2B, FIG. 3, FIGS. 4A and 4B, and FIGS. 5A and 5B.

Figure 1B:
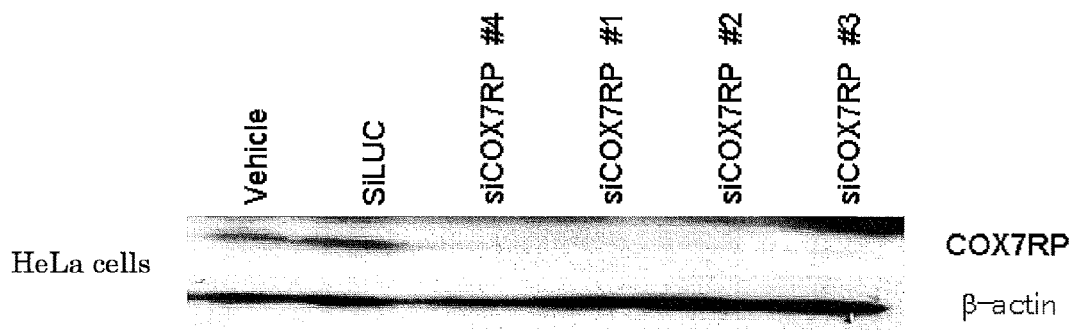
FIG. 1B is a western blot image which shows the suppressive effect of each siCOX7RP on the expression of COX7RP in HeLa cells.
Figure 1C:
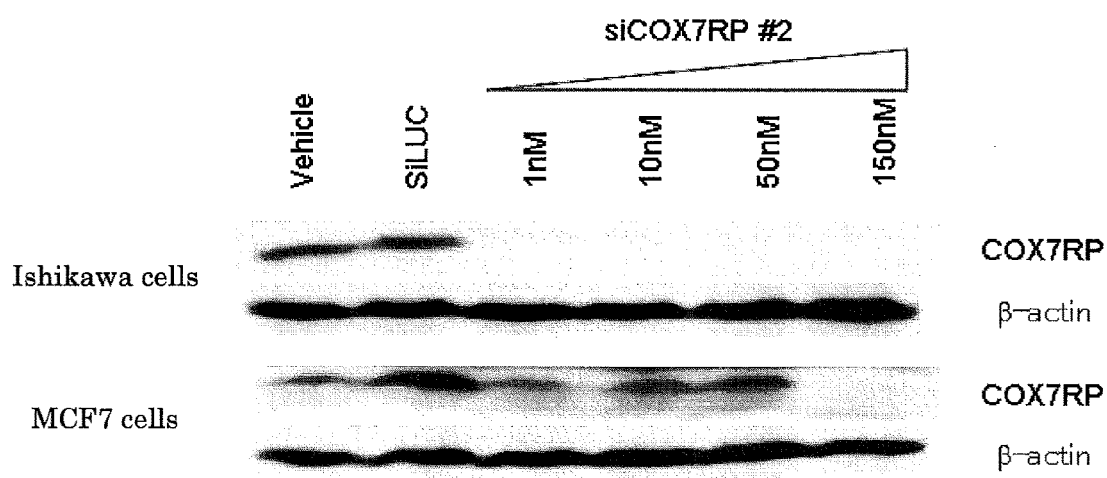
FIG. 1C is a western blot image which shows the suppressive effect of siCOX7RP#2 on the expression of COX7RP in Ishikawa and MCF7 cells.

In Ishikawa cells, sequences #1 and #2 were found to have a remarkably high knockdown effect on the expression of COX7RP; and the knockdown effect of sequence #5 was found to be high next to these sequences, and that of sequence #3 was found to be relatively poor (FIG. 1A). In HeLa cells, all the tested four sequences #1 to #4 were found to have a remarkably high knockdown effect (FIG. 1B). Of these, the knockdown effect of sequence #2 was particularly high. Specifically, in MCF7 cells, the band indicating the expression of COX7RP completely disappeared only at a concentration of 150 nM; and, in Ishikawa cells, that band completely disappeared even at a concentration of 1 nM, confirming that sequence #2 exhibited a strong knockdown effect (FIG. 1C).

Figure 2A:
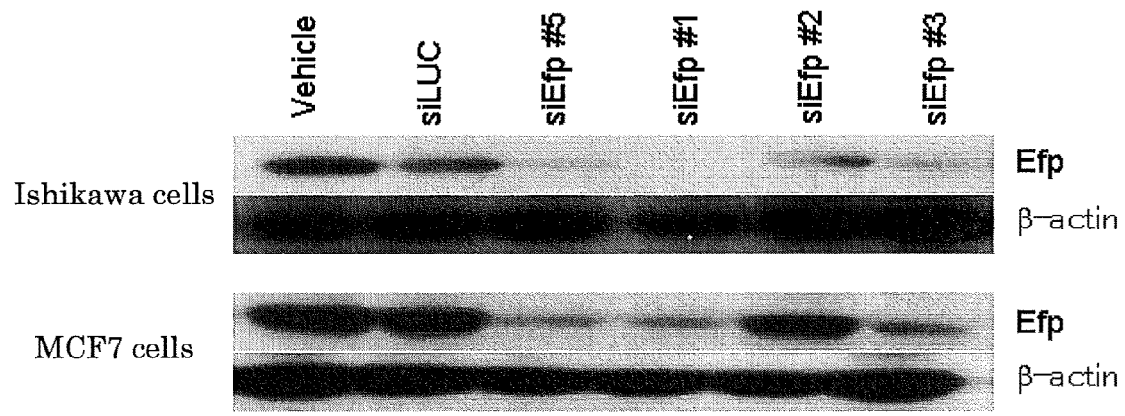
FIG. 2A is a western blot image which shows the suppressive effect of each siEfp on the expression of Efp in Ishikawa and MCF7 cells.
Figure 2B:
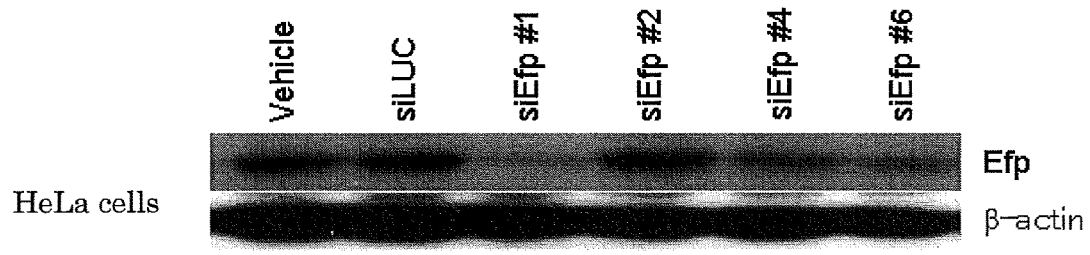
FIG. 2B is a western blot image which shows the suppressive effect of each siEfp on the expression of Efp in HeLa cells.

Meanwhile, on the expression of Efp, sequences #1, #5, #3 and #2 were found to have a knockdown effect increasing in the order mentioned in Ishikawa cells and MCF7 cells (FIG. 2A). In HeLa cells, the knockdown effect of sequence #1 was also high, and the knockdown effects of sequences #4 and #6 were not lower than that of sequence #2 but were slightly inferior to that of sequence #1 (FIG. 2B).

Figure 3:
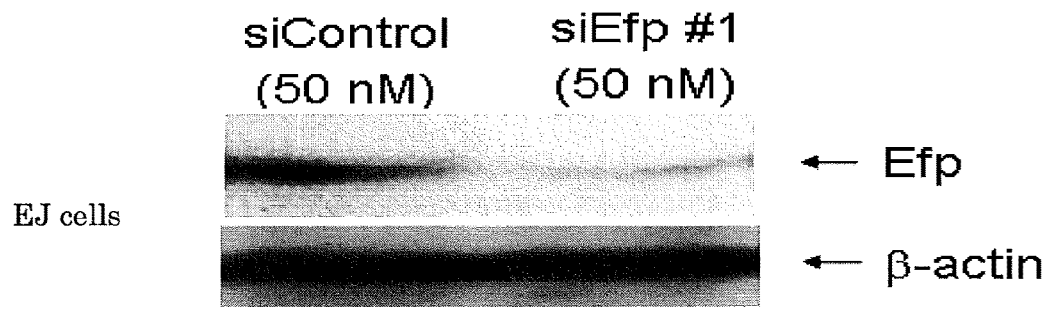
FIG. 3 is a western blot image which shows the suppressive effect of siEfp#1 on the expression of Efp in EJ cells.

Further, siEfp#1 was found to effectively suppress the expression of Efp even in EJ cells (bladder cancer cells); i.e., to have a high knockdown effect (FIG. 3).

Figure 4A:
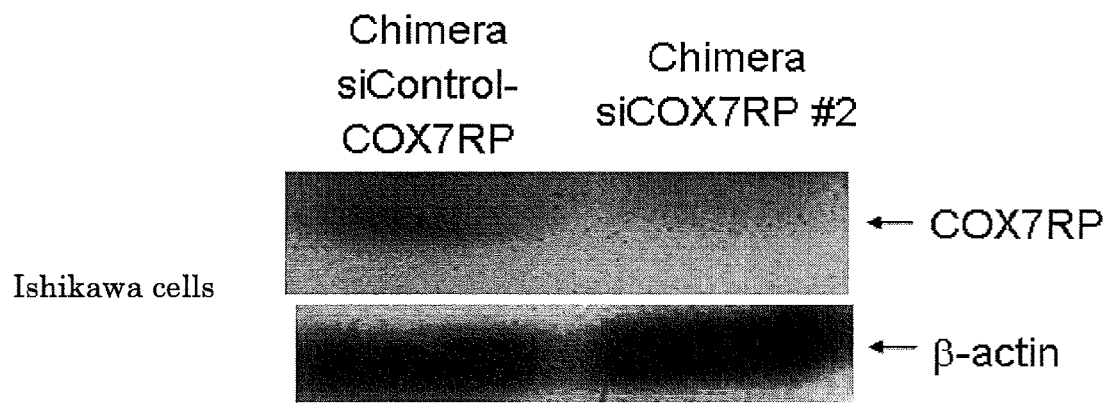
FIG. 4A is a western blot image which shows the suppressive effect of chimera siCOX7RP#2 on the expression of COX7RP in Ishikawa cells.
Figure 4B:
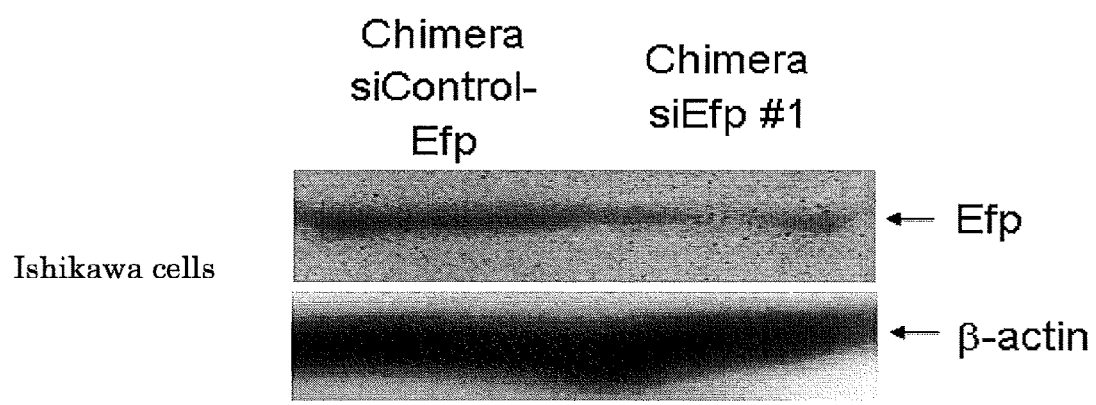
FIG. 4B is a western blot image which shows the suppressive effect of chimera siEfp#1 on the expression of Efp in Ishikawa cells.
Figure 5A:
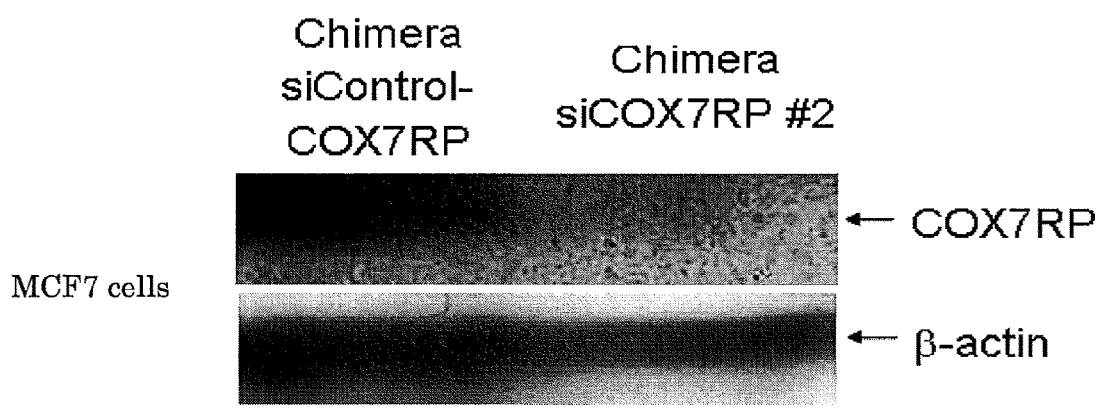
FIG. 5A is a western blot image which shows the suppressive effect of chimera siCOX7RP#2 on the expression of COX7RP in MCF7 cells.
Figure 5B:
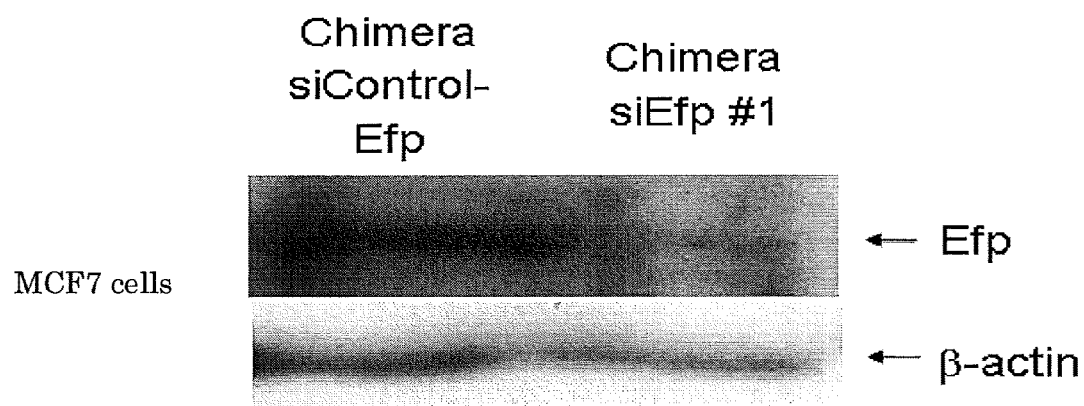
FIG. 5B is a western blot image which shows the suppressive effect of chimera siEfp#1 on the expression of Efp in MCF7 cells.

Chimera siRNAs (chimera siCOX7RP#2 and chimera siEfp#1) corresponding to the siRNAs (siCOX7RP#2 and siEfp#1) having a high knockdown effect were found to effectively suppress the expressions of COX7RP and Efp in both Ishikawa cells and MCF7 cells (Ishikawa cells: FIGS. 4A and 4B, and MCF7 cells: FIGS. 5A and 5B).

Example 4

Study on the Inhibitory Effect of siRNA and Chimera siRNA on Cell Proliferation In Vitro Each of the siRNAs obtained in Example 1 and the chimera siRNAs obtained in Example 2 was transfected into culture cells derived from human uterine, breast and bladder cancers (Ishikawa cells, MCF7 cells and EJ cells), to thereby study the inhibitory effect of the siRNA and chimera siRNA on the proliferation of the culture cells. The detail description of the experimental method is given below. Notably, the cells were cultured in the same manner as in Example 3.

[Transfection and Cell Counting]

On the day before transfection, 8,000 Ishikawa cells, 8,000 MCF7 cells and 6,000 EJ cells were placed in a 24-well plate. Subsequently, Opti-MEM (Gibco) (250 L/well) and Lipofectamine 2000 (Invitrogen) (10 µL/well) was mixed with each other, followed by incubating for 5 min at 37° C. The resultant mixture was added to a mixture of Opti-MEM (250 µL/well) and siRNA (final concentration: 50 nM), followed by further incubating at 37° C. for 20 min. The resultant mixture was added to the wells. Notably, in the case of chimera siRNA, the final concentration was set to 150 nM. One to seven days after the addition of the siRNA or chimera siRNA, the cells were treated for coloring with living cell counting reagent SF (Cell Count Reagent SF, NACALAI TESQUE, INC.), and then measured for absorbance (450 nm) for quantification of cell count.

The results of Example 4 are shown in FIGS. 6A and 6B, FIGS. 7A and 7B, FIG. 8, FIGS. 9A and 9B, and FIGS. 10A and 10B.

Figure 6A:
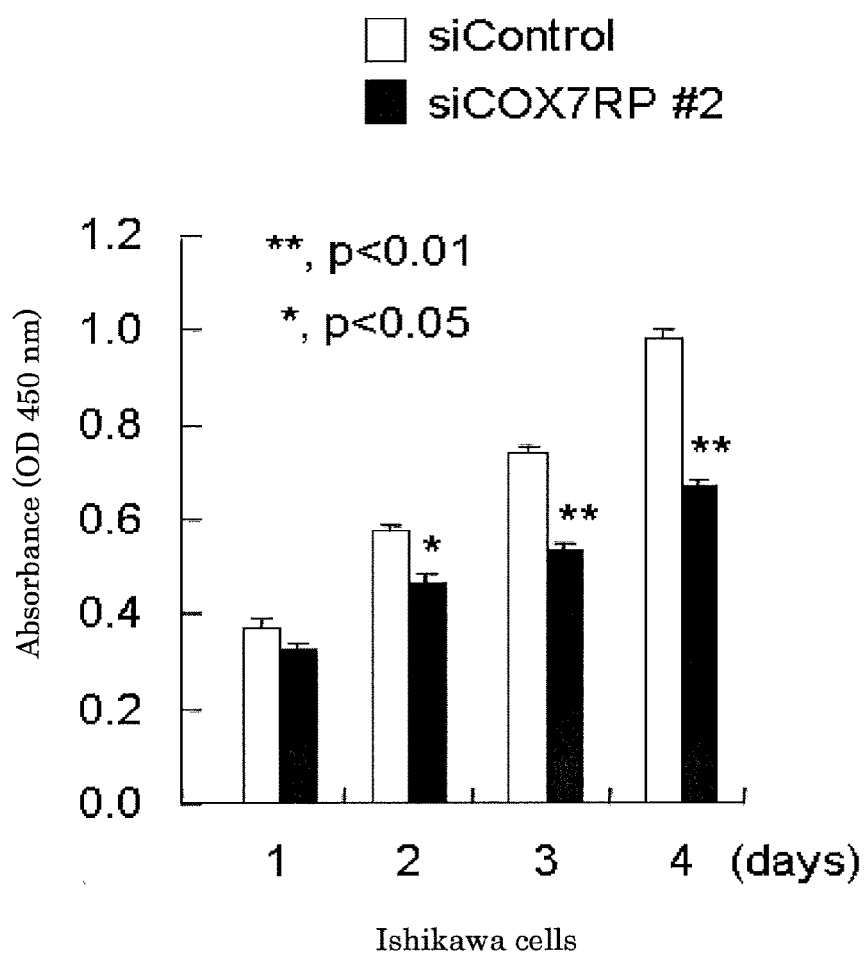
FIG. 6A is a graph which shows the inhibitory effect of siCOX7RP#2 on the proliferation of Ishikawa cells.
Figure 6B:
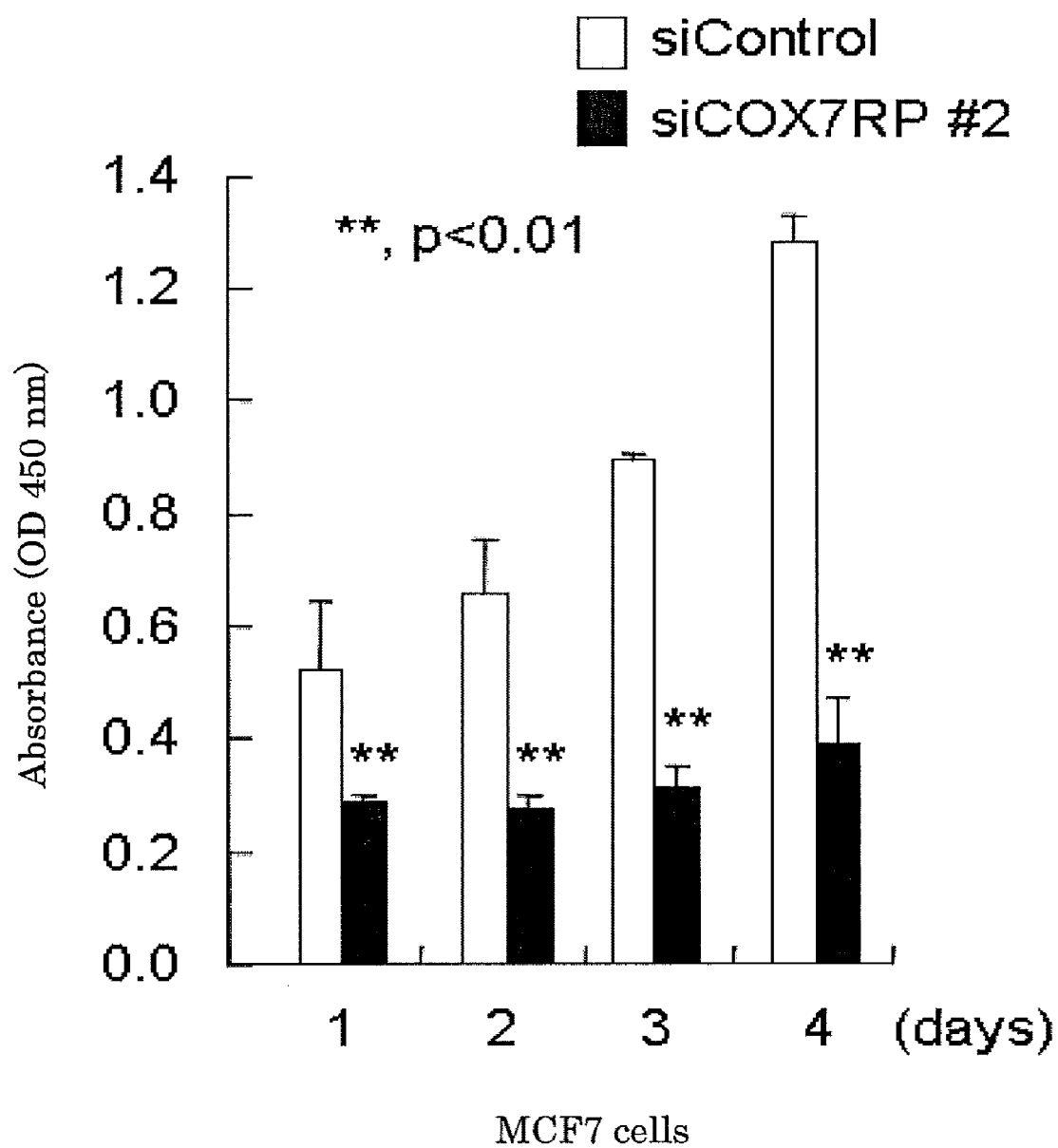
FIG. 6B is a graph which shows the inhibitory effect of siCOX7RP#2 on the proliferation of MCF7 cells.
Figure 7A:
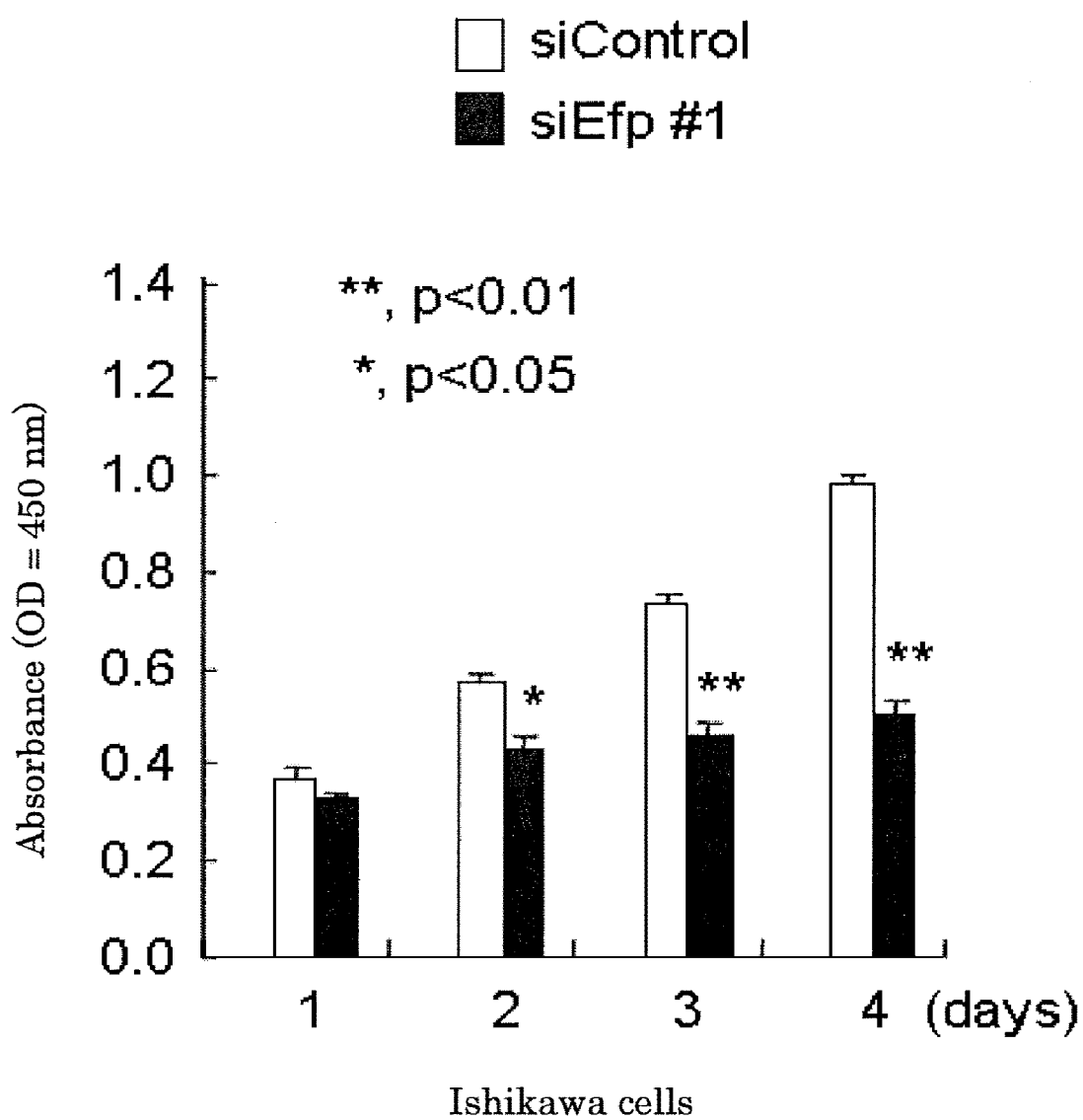
FIG. 7A is a graph which shows the inhibitory effect of siEfp#1 on the proliferation of Ishikawa cells.

After each of siCOX7RP#2, siEfp#1 and siControl had been transfected into Ishikawa cells and MCF7 cells, the cell proliferation rate was analyzed. As a result, siCOX7RP#2 and siEfp#1 were found to significantly inhibit the proliferation of Ishikawa cells from Day 2, and to significantly inhibit the proliferation of MCF7 cells from Day 1 (siCOX7RP#2: FIGS. 6A and 6B and siEfp#1: FIGS. 7A and 7B).

Figure 8:
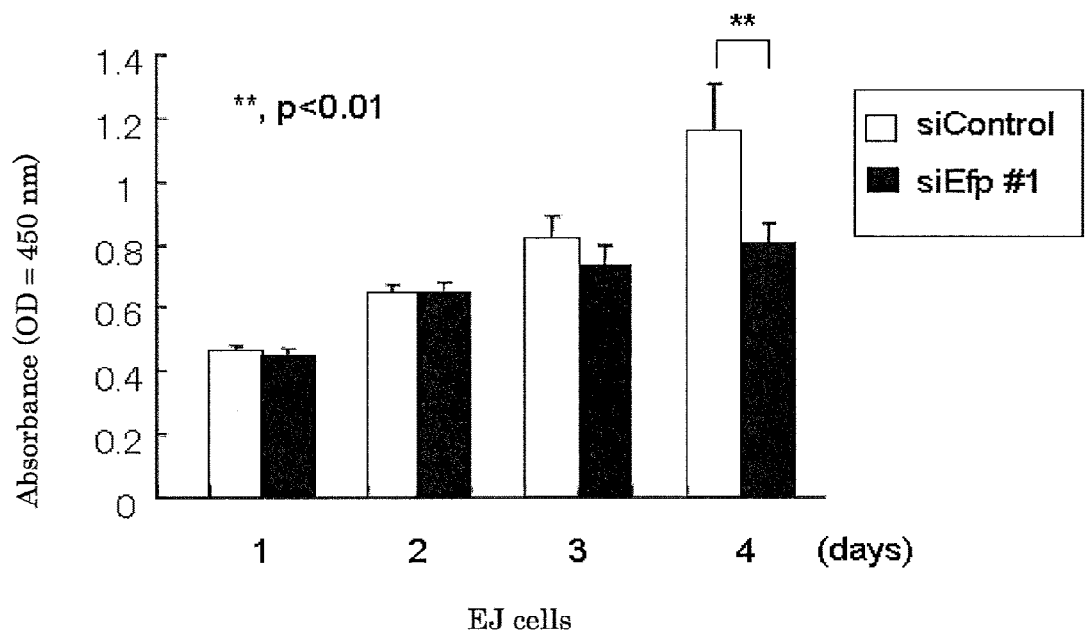
FIG. 8 is a graph which shows the inhibitory effect of siEfp#1 on the proliferation of EJ cells.

Similarly, after siEfp#1 and siControl had been transfected into EJ cells, the cell proliferation rate was analyzed. As a result, siEfp#1 was found to significantly inhibit the proliferation of the cells on Day 4 (FIG. 8).

Figure 9A:
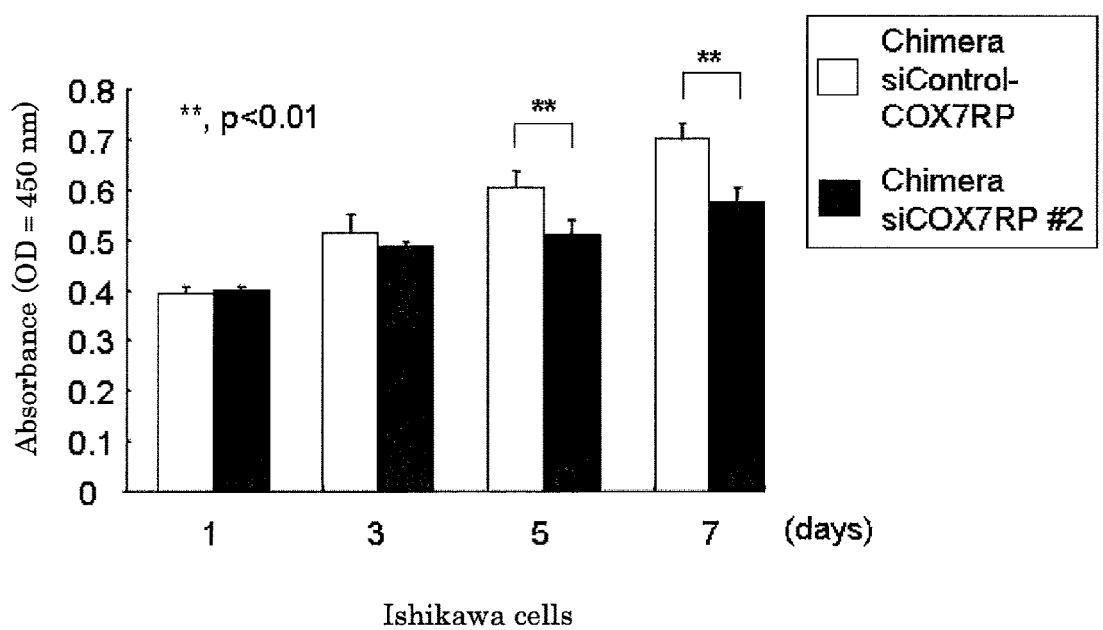
FIG. 9A is a graph which shows the inhibitory effect of chimera siCOX7RP#2 on the proliferation of Ishikawa cells.
Figure 9B:
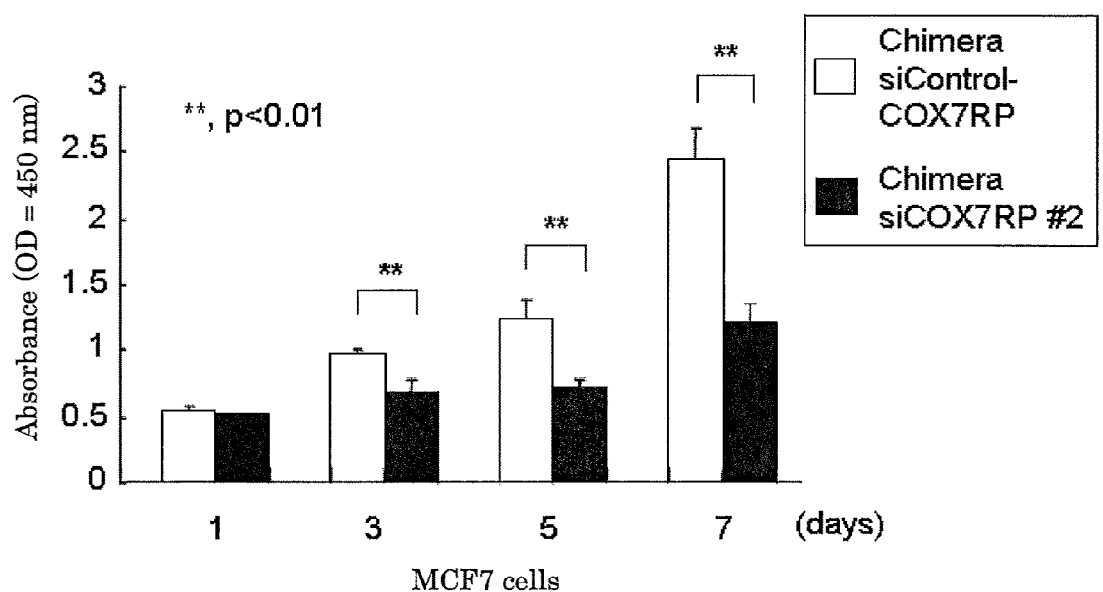
FIG. 9B is a graph which shows the inhibitory effect of chimera siCOX7RP#2 on the proliferation of MCF7 cells.
Figure 10A:
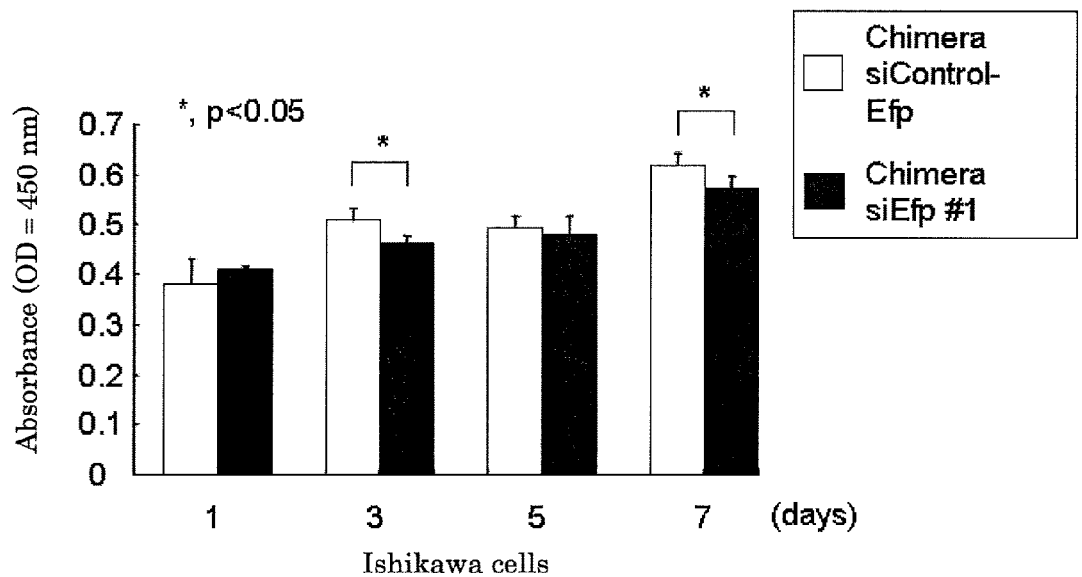
FIG. 10A is a graph which shows the inhibitory effect of chimera siEfp#1 on the proliferation of Ishikawa cells.
Figure 10B:
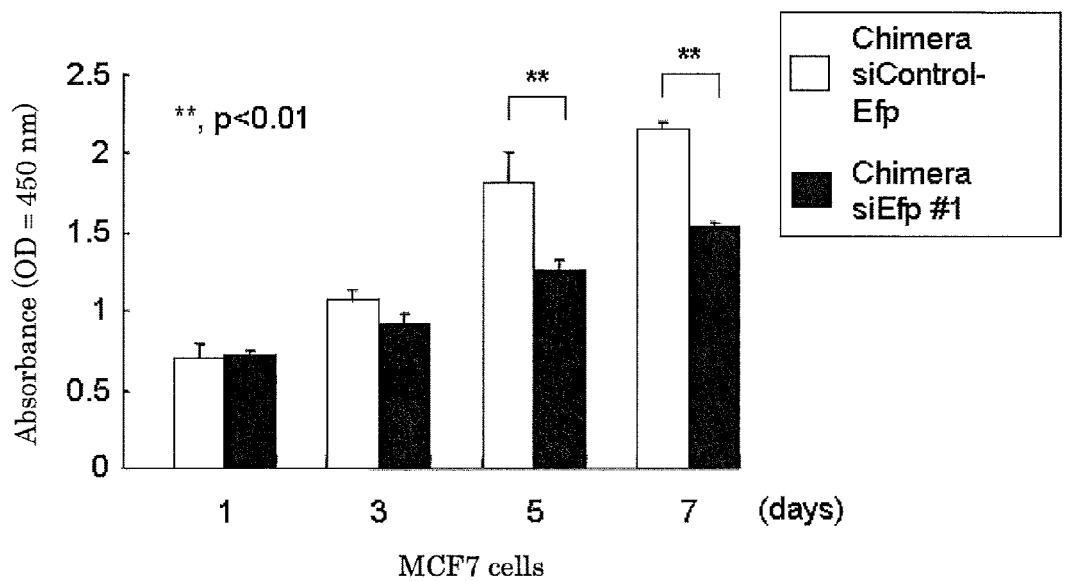
FIG. 10B is a graph which shows the inhibitory effect of chimera siEfp#1 on the proliferation of MCF7 cells.

After chimera siRNAs (chimera siCOX7RP#2 and chimera siEfp#1) had been transfected into Ishikawa cells and MCF7 cells, the cell proliferation rate was analyzed. As a result, chimera siCOX7RP#2 and chimera siEfp#1 were found to significantly inhibit the proliferation of the cells (chimera siCOX7RP#2: FIGS. 9A and 9B and chimera siEfp#1: FIGS. 10A and 10B).

Example 5

Study on the Inhibitory Effect of siRNA and Chimera siRNA on Tumor Growth In Vivo Each of the siRNAs obtained in Example 1 and the chimera siRNAs obtained in Example 2 was studied on the proliferation inhibitory effect on tumor cells which were subcutaneously transplanted in a nude mouse. The detail description of the experimental method is given below. Notably, cell culture and western blot analysis were performed in the same manner as in Example 3.

[Experiment on Tumor Growth Inhibition In Vivo (siRNA/Ishikawa Cells and MCF7 Cells)]

Four-week-old female nude mice BALB/cA Jcl-nu (CLEA Japan, Inc.) were provided (12 mice for each group), and tumor cells were subcutaneously transplanted into these mice. The transplanted cells were prepared by mixing Ishikawa cells ($2 \times 10^7$ cells/mouse) or MCF7 cells ($1 \times 10^7$ cells/mouse) with Matrigel (BD Biosciences) so that the total amount was adjusted to 150 µL/mouse. The tumor radii of each mouse were measured twice in a week, and used to calculate tumor volume ($3 \cdot r^3/4$, where r=major radius×minor radius×minor radius/8).

From week 1.5 after transplantation, siCOX7RP or siEfp was injected directly into the subcutaneously transplanted tumor of each mouse at twice in a week. Notably, the siCOX7RP and siEfp used were respectively siCOX7RP#2 and siEfp#1 which were found to have a high knockdown effect in Example 2. The sample injected into the mouse was prepared by mixing each siRNA (5 µg/mouse) with GeneSilencer Reagent (Gene Therapy Systems, Inc.) (4 µL/mouse) and phenol red free DMEM so that the total amount was adjusted to 50 µL/mouse.

At week 7.5 after transplantation, each nude mouse was killed and then the subcutaneous tumor thereof was taken and homogenized with Homogenize Buffer (100 mM Tris-Hcl, pH 7.4, 250 mM sucrose and 1 mM PMSF). Further, the homogenized product was mixed with 4× Sample Buffer, followed by boiling at 100° C. for 15 min. Thereafter, the resultant protein sample (1,000 µg) was analyzed through western blotting.

[Experiment on Tumor Growth Inhibition In Vivo (siRNA/EJ Cells)]

Four-week-old male nude mice BALB/cA Jcl-nu (CLEA Japan, Inc.) were provided (10 mice for each group), and EJ cells were subcutaneously transplanted into these mice. The transplanted cells were prepared by mixing EJ cells ($1 \times 10^6$ cells/mouse) with Matrigel (BD Biosciences) so that the total amount was adjusted to 150 µL/mouse. From week 1 after transplantation, siEfp#1 and siControl were each treated similar to the above and then directly injected into the subcutaneous tumor of each mouse twice in a week. The tumor radii of the mouse were measured twice in a week, and used to calculate tumor volume ($3 \cdot r^3/4$, where r=major radius× minor radius×minor radius/8).

[Experiment on Tumor Growth Inhibition In Vivo (Chimera siRNA/Ishikawa Cells)]

Four-week-old female nude mice BALB/cA Jcl-nu (CLEA Japan, Inc.) were provided (10 mice for each group), and tumor cells were subcutaneously transplanted into these mice. The transplanted cells were prepared by mixing Ishikawa cells ($4 \times 10^6$ cells/mouse) with Matrigel (BD Biosciences) so that the total amount was adjusted to 150 μL/mouse. From week 1 after transplantation, chimera siCOX7RP#2, chimera siEfp#1, chimera siControl-COX7RP and chimera siControl-Efp were each treated similar to the above and then directly injected into the subcutaneous tumor of each mouse twice in a week. The tumor radii of the mouse were measured twice in a week, and used to calculate tumor volume ($3 \cdot r^3/4$, where r=major radius×minor radius×minor radius/8).

At week 5.5 after transplantation, each nude mouse was killed and then the subcutaneous tumor thereof was taken and homogenized with Homogenize Buffer (100 mM Tris-Hcl, pH 7.4, 250 mM sucrose and 1 mM PMSF). Further, the homogenized product was mixed with 4× Sample Buffer, followed by boiling at 100° C. for 15 min. Thereafter, the resultant protein sample (1,000 μg) was analyzed through western blotting.

The results of Example 5 are shown in FIGS. 11A to 11C, FIGS. 12A to 12C, FIGS. 13A and 13B, FIGS. 14A to 14C, and FIG. 15A to 15C.

Figure 11A:
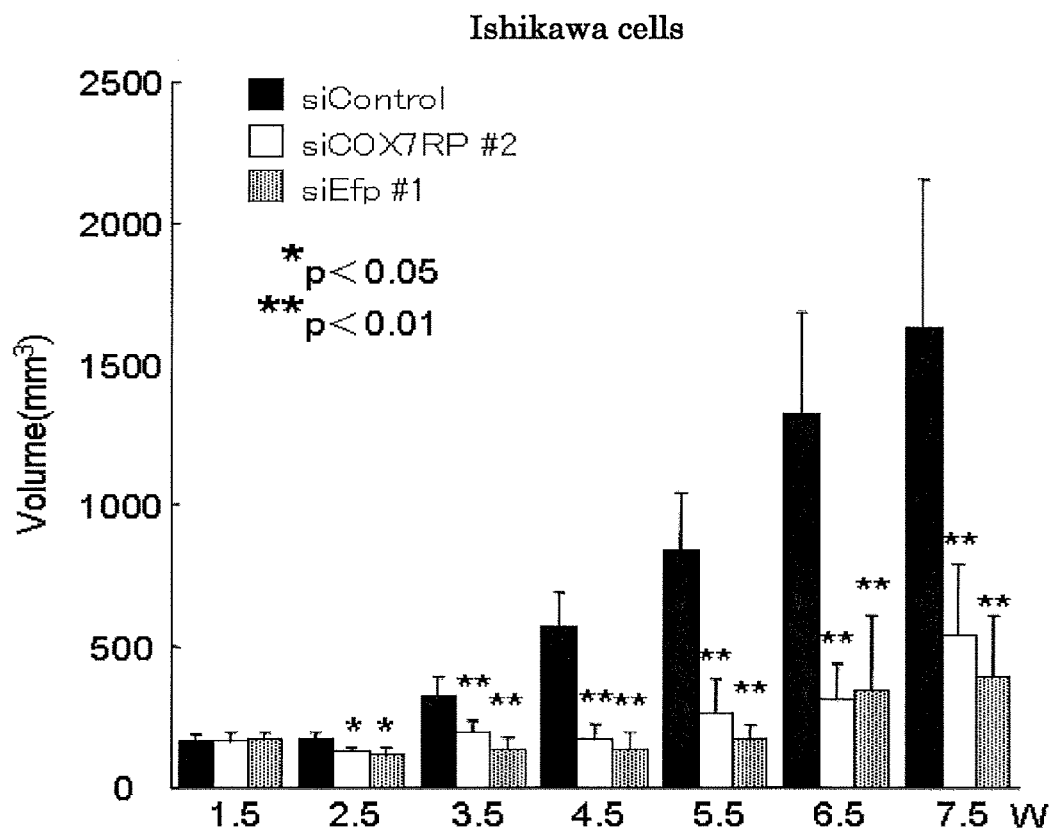
FIG. 11A is a graph which shows the inhibitory effect of each siRNA on increase in tumor volume of mice into which Ishikawa cells have subcutaneously been transplanted.
Figure 11B:
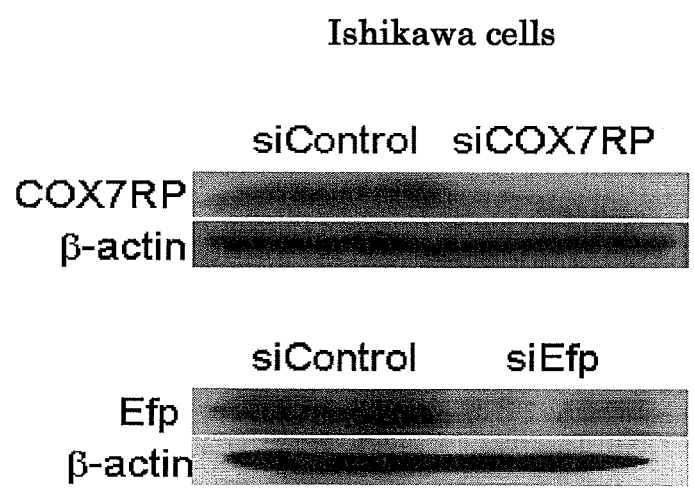
FIG. 11B gives western blot images which show the suppressive effect of each siRNA on the expression of COX7RP or Efp at week 7.5 after transplantation of Ishikawa cells.
Figure 11C:
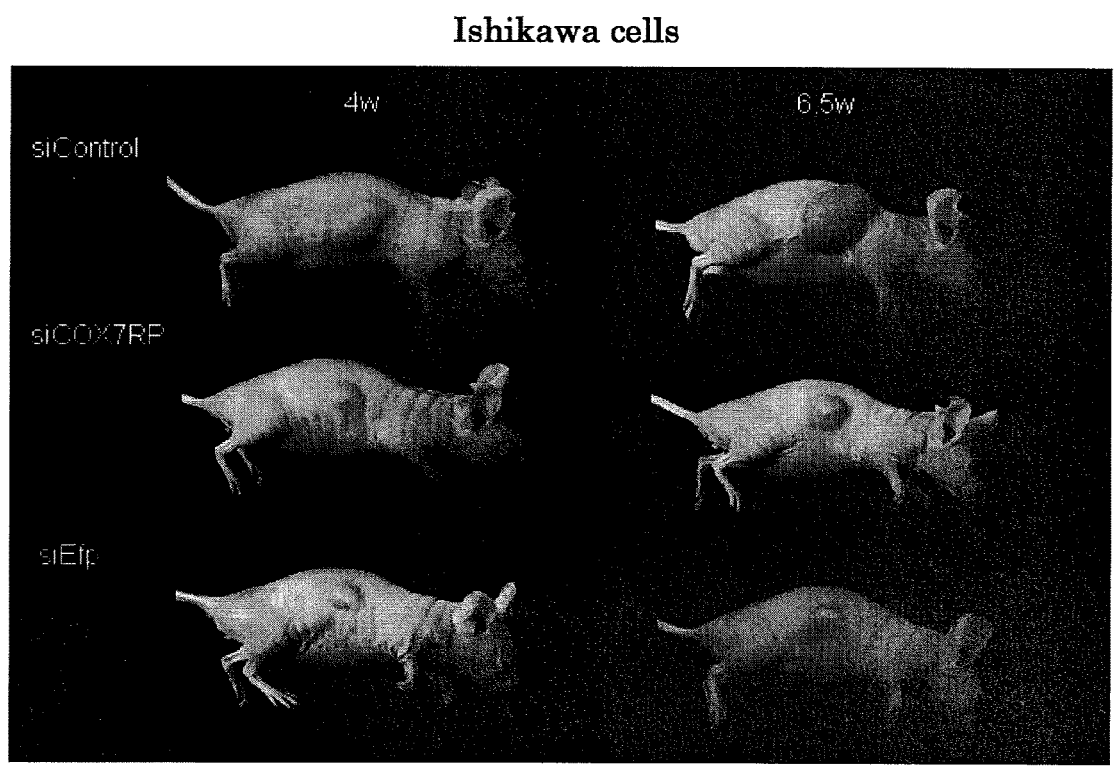
FIG. 11C is a photograph of mice of the respective siRNA administration groups at week 4 or 6.5 after transplantation of Ishikawa cells.

In Ishikawa cells, the tumor volume in the siControl group was exponentially increased, while that in both the siCOX7RP and siEfp groups was reduced at week 2.5 after transplantation and then moderately increased. Finally, at week 7.5 after transplantation, the tumor volume in these administration groups was found to be about a third of that in the mice of the siControl group. Through Student's t-test for comparing each of the siCOX7RP and siEfp groups with the siControl group in terms of the tumor volume, a significant difference of $p<0.05$ was observed at week 2.5 after transplantation and a significant difference of $p<0.01$ from week 3.5 after transplantation (FIG. 11A). Also, when the expression levels of COX7RP and Efp in the subcutaneous tumor were analyzed through western blotting after week 7.5 after transplantation, these expression levels were found to be decreased in both the siCOX7RP and siEfp groups (FIG. 11B, in which two samples are shown for each group). FIG. 11C shows photographs of the actual nude mice of the respective groups (one mouse/group), which were taken at week 4 or 6.5 after transplantation. As is clear from these photographs, the tumor growth in both the siCOX7RP and siEfp groups is inhibited as compared to the siControl group.

Figure 12A:
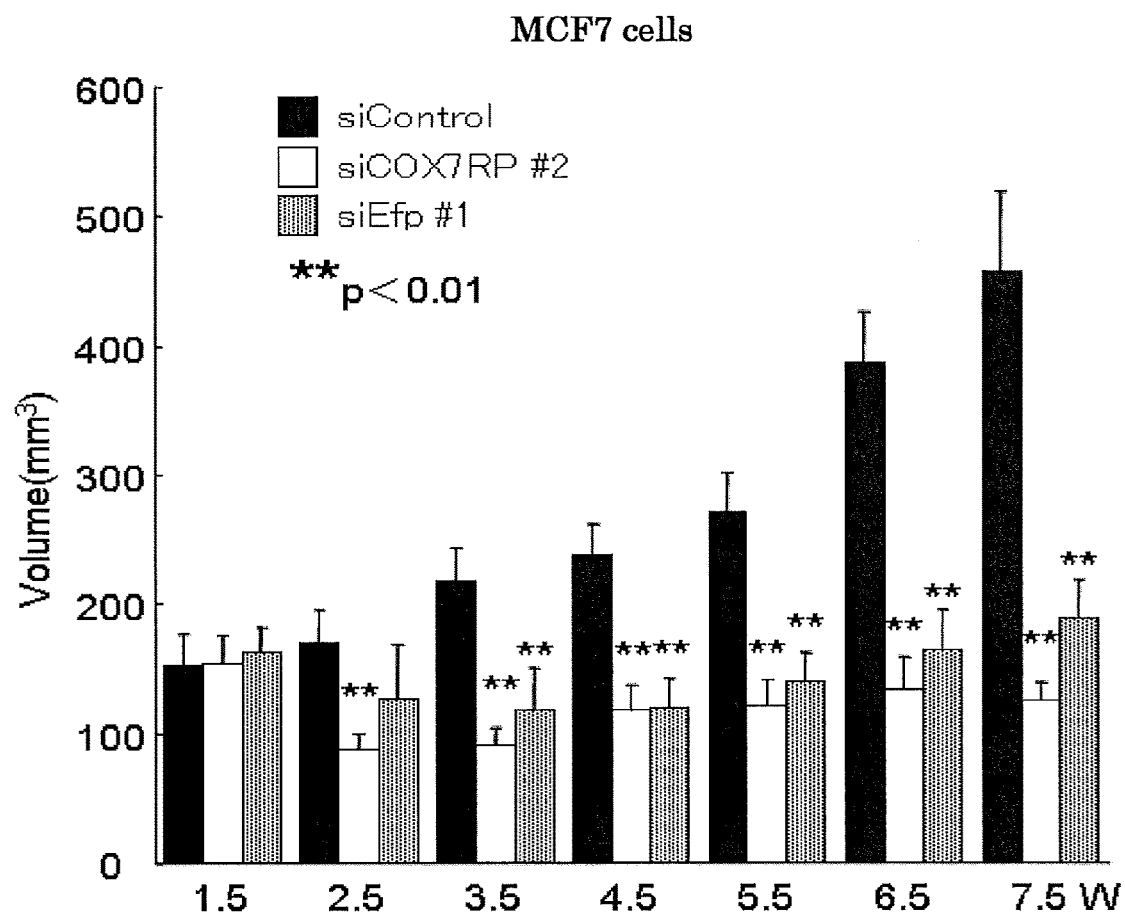
FIG. 12A is a graph which shows the inhibitory effect of each siRNA on increase in tumor volume of mice into which MCF7 cells have subcutaneously been transplanted.
Figure 12B:
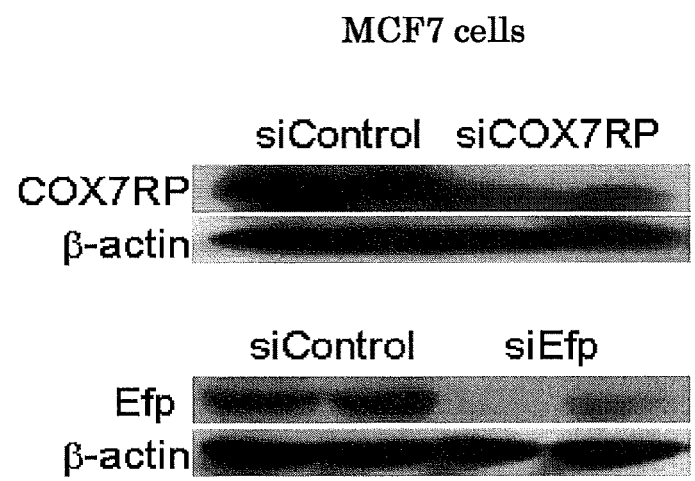
FIG. 12B gives western blot images which show the suppressive effect of each siRNA on the expression of COX7RP or Efp at week 7.5 after transplantation of MCF7 cells.
Figure 12C:
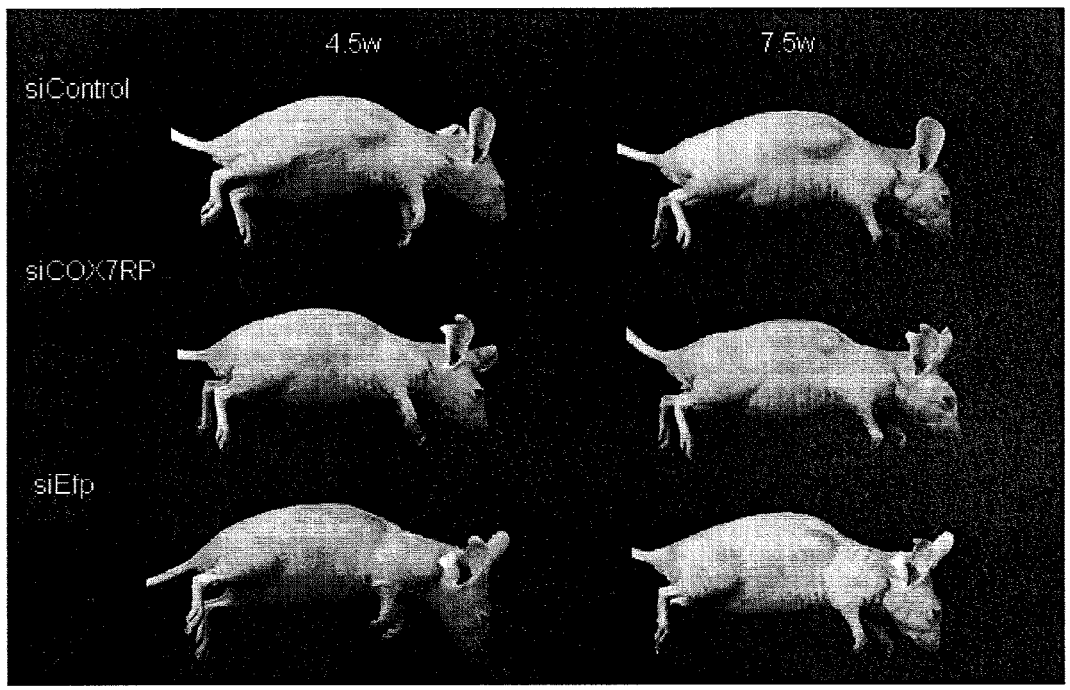
FIG. 12C is a photograph of mice of the respective siRNA administration groups at week 4 or 6.5 after transplantation of MCF7 cells.

The similar analysis was performed on MCF7 cells. At week 2.5 after transplantation, the mice of both the siCOX7RP and siEfp groups were reduced in tumor volume. The tumor volume in the mice of the siCOX7RP group was not increased much after that. Also in the siEfp group, the tumor volume at week 7.5 after transplantation was merely slightly different from that at week 1.5 after transplantation. Through Student's t-test, the knockdown effect was significantly observed ($p<0.01$) in the siCOX7RP group from week 2.5 after transplantation and in the siEfp group from week 3.5 after transplantation (FIG. 12A). Also, in the subcutaneous tumor after week 7.5 after transplantation, the expression levels of COX7RP and Efp were decreased by the action of siCOX7RP and siEfp (FIG. 12B). FIG. 12C shows photographs of the actual nude mice of the respective groups (one mouse/group), which were taken at week 4.5 or 7.5 after transplantation. As is clear from these photographs, the tumor growth in both the siCOX7RP and siEfp groups is inhibited as compared to the siControl group.

Figure 13A:
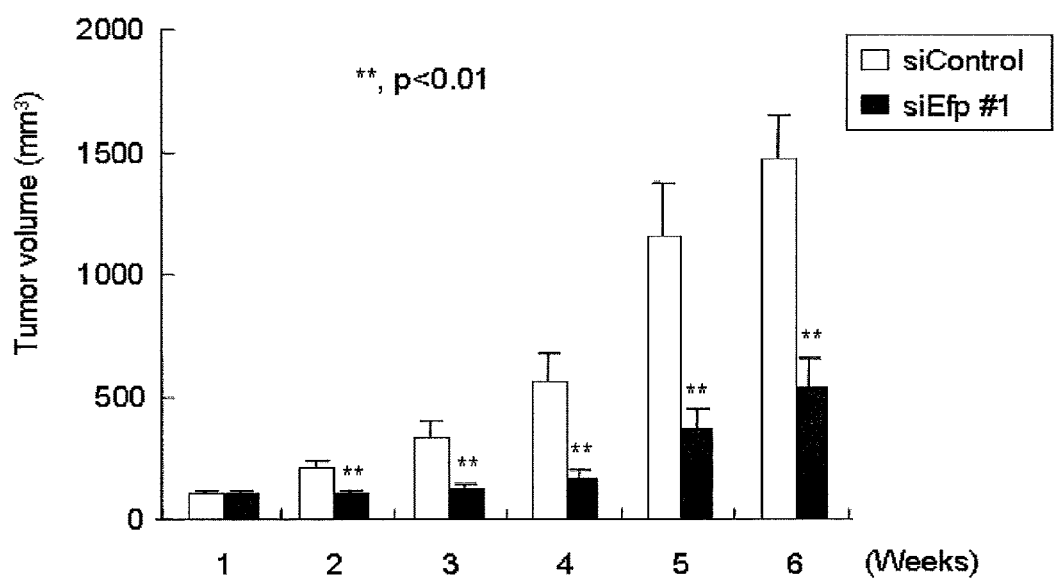
FIG. 13A is a graph which shows the inhibitory effect of siEfp#1 on increase in tumor volume of mice into which EJ cells have subcutaneously been transplanted.
Figure 13B:
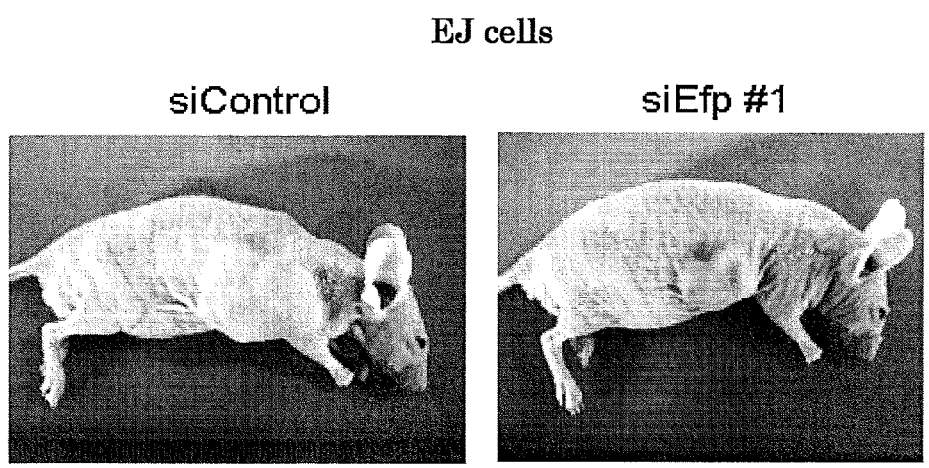
FIG. 13B gives photographs of mice of the respective siRNA administration groups at week 4.5 after transplantation of EJ cells.

The similar analysis was performed on EJ cells. As a result, the knockdown effect was significantly observed ($p<0.01$) in the siEfp#1 group from week 2 after transplantation, clearly indicating that siEfp#1 effectively inhibited the tumor growth even in a nude mouse tumor growth model using EJ cells (bladder cancer cells) (FIG. 13A). FIG. 13B shows photographs of the actual nude mice of the respective groups (one mouse/group), which were taken at week 4.5 after transplantation. As is clear from these photographs, the tumor growth in the siEfp#1 group is inhibited as compared to the siControl group.

Figure 14A:
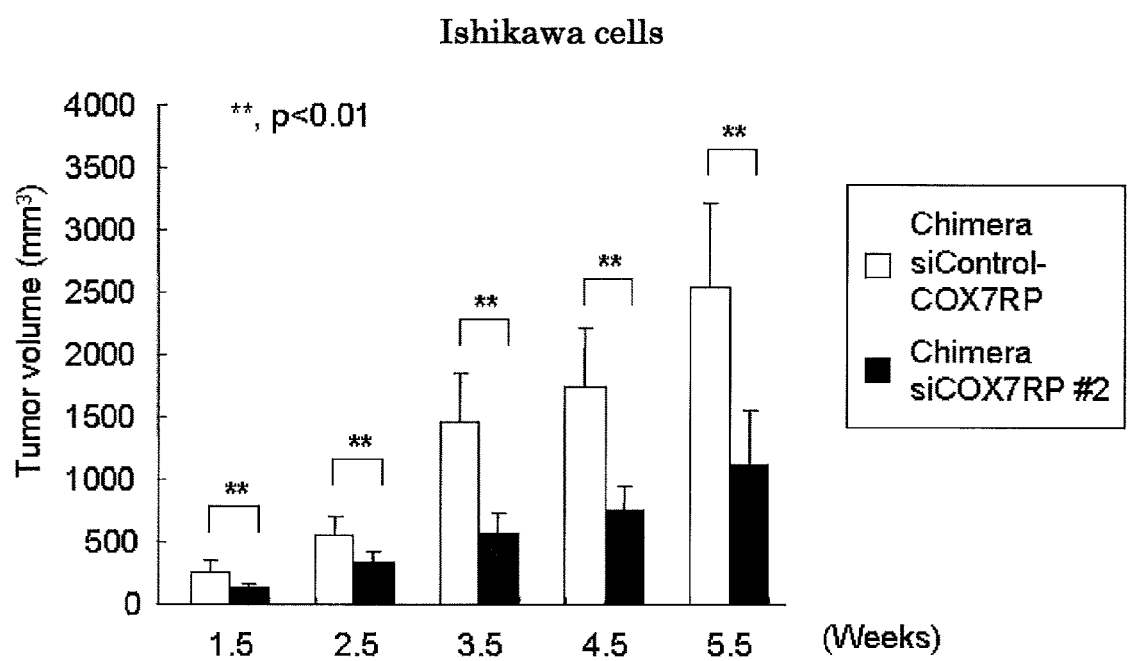
FIG. 14A is a graph which shows the inhibitory effect of chimera siCOX7RP#2 on increase in tumor volume of mice into which Ishikawa cells have subcutaneously been transplanted.
Figure 14B:
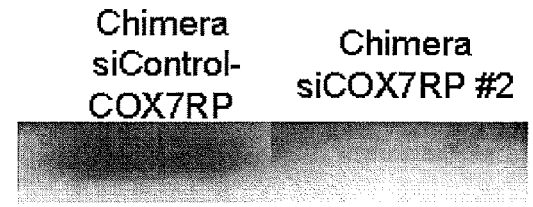
FIG. 14B is a western blot image which shows the suppressive effect of chimera siCOX7RP#2 on the expression of COX7RP at week 5.5 after transplantation of Ishikawa cells.
Figure 14C:
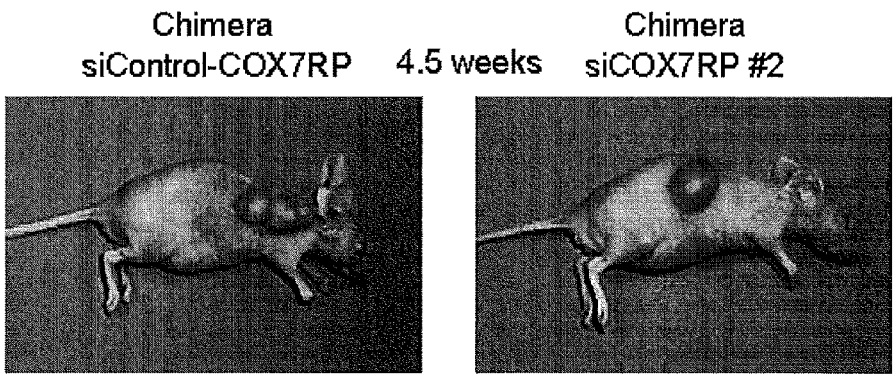
FIG. 14C gives photographs of mice of the respective chimera siRNA administration groups at week 4.5 after transplantation of Ishikawa cells.

Also, the similar analysis was performed using chimera siRNA. In Ishikawa cells, the tumor volume in the chimera siControl-COX7RP group was exponentially increased, while increase of the tumor volume in the chimera siCOX7RP#2 was significantly suppressed (FIG. 14A). Also, in the subcutaneous tumor at week 5.5 after transplantation, the expression level of COX7RP was decreased by the action of chimera siCOX7RP#2 (FIG. 14B). FIG. 14C shows photographs of the actual nude mice of the respective groups (one mouse/group), which were taken at week 4.5 after transplantation. As is clear from these photographs, the tumor growth in the chimera siCOX7RP#2 group is inhibited as compared to the chimera siControl-COX7RP group.

Figure 15A:
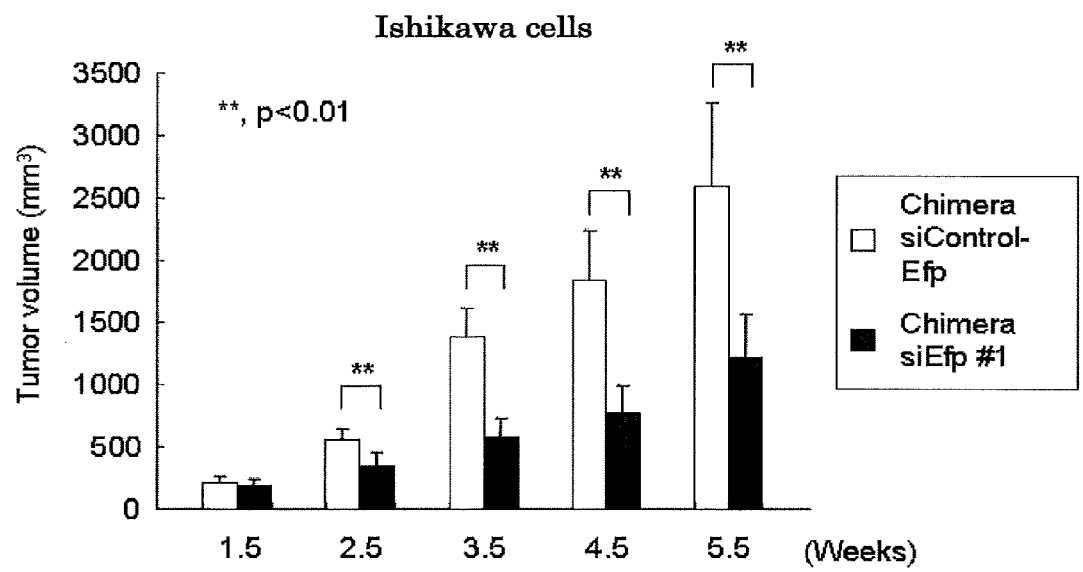
FIG. 15A is a graph which shows the inhibitory effect of chimera siEfp#1 on increase in tumor volume of mice into which Ishikawa cells have subcutaneously been transplanted.
Figure 15B:
FIG. 15B is a western blot image which shows the suppressive effect of chimera siEfp#1 on the expression of Efp at week 5.5 after transplantation of Ishikawa cells.
Figure 15C:
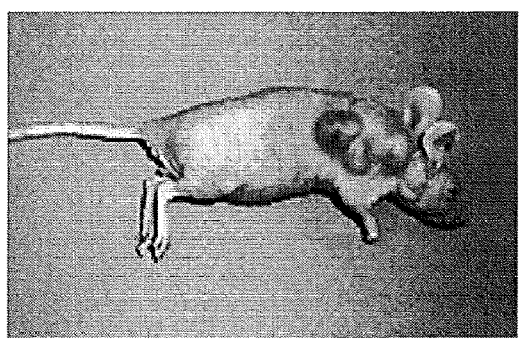
FIG. 15C gives photographs of mice of the respective chimera siRNA administration groups at week 4.5 after transplantation of Ishikawa cells.
Figure 15C:

Similarly, in Ishikawa cells, the tumor volume in the chimera siControl-Efp group was exponentially increased, while increase of the tumor volume in the chimera siEfp#1 group was significantly suppressed (FIG. 15A). Also, in the subcutaneous tumor at week 5.5 after transplantation, the expression level of Efp was decreased by the action of chimera siEfp#1 (FIG. 15B). FIG. 15C shows photographs of the actual nude mice of the respective groups (one mouse/group), which were taken at week 4.5 after transplantation. As is clear from these photographs, the tumor growth in the chimera siEfp#1 group is inhibited as compared to the chimera siControl-Efp group.

From the above-described Examples 1 to 5, the double-stranded nucleic acid molecules (siRNAs) of the present invention were found to have a high suppressive effect on the expressions of COX7RP and Efp genes in uterine, breast and bladder cancer cells. Also, the double-stranded nucleic acid molecules were found to have a high tumor growth inhibitory effect even in vivo and thus, are presumably suitable to an active ingredient of the pharmaceutical agent for the prevention or treatment of uterine, breast and bladder cancers. In particular, siCOX7RP#2 exhibited the knockdown effect to a sufficient extent in Ishikawa cells at a concentration of as low as 1 nM (FIG. 1C) and thus, is expected to be clinically used for the treatment of uterine cancer including endometrial cancer.

The results of Examples clearly indicate that both the chimera siCOX7RP and the chimera siEfp, which were respectively designed on the basis of the sequences of the corresponding siRNAs, could also function as an siRNA having a high knockdown effect. In addition, from the results obtained by confirming whether or not these could inhibit the tumor growth in vivo, the tumor formed was found to be significantly smaller in the chimera siCOX7RP or chimera siEfp administration group than in the control group. Thus, similar to siRNAs, these chimera siRNAs are suggested to have a possibility of being clinically applied to the treatment of uterine, breast and bladder cancers. The chimera siRNAs (i.e., double-stranded RNA-DNA chimeras) are advantageously practically applied to clinical use, since they are, for example, highly stable in blood, involve low immune response induction, and are produced at low cost.

INDUSTRIAL APPLICABILITY

The double-stranded nucleic acid molecule of the present invention can effectively inhibit the proliferation of uterine, breast and bladder cancer cells by suppressing the expression of at least one of COX7RP and Efp genes (estrogen-responsive genes) and thus, is useful for an active ingredient of a pharmaceutical agent against uterine, breast and bladder cancers. Also, the pharmaceutical agent containing as an active ingredient the double-stranded nucleic acid molecule of the present invention acts, in the estrogen pathway, at a stage more downstream of that where conventional drugs such as tamoxifen acting on an estrogen receptor acts and thus, is expected to be a pharmaceutical agent with a lower degree of adverse side effects.

What is claimed is:

1. A double-stranded nucleic acid molecule comprising:
   (a) a sense strand which comprises a nucleotide sequence corresponding to a target sequence indicated by any one of SEQ ID Nos.: 1 to 38, and
   (b) an antisense strand which comprises a nucleotide sequence complementary to that of the sense strand specified in (a),
   wherein the double-stranded nucleic acid molecule is for suppressing the expression of at least one of COX7RP and estrogen-responsive finger protein (Efp) genes.

2. The double-stranded nucleic acid molecule according to claim 1, wherein the sense strand has a nucleotide sequence which corresponds to a target sequence indicated by any one of SEQ ID Nos.: 1 to 5 and 16 to 21.

3. The double-stranded nucleic acid molecule according to claim 2, wherein the sense strand has a nucleotide sequence which corresponds to a target sequence indicated by any one of SEQ ID Nos.: 1, 2, 4, 5, 16, 18, 19, 20 and 21.

4. The double-stranded nucleic acid molecule according to claim 3, wherein the sense strand has a nucleotide sequence which corresponds to a target sequence indicated by any one of SEQ ID Nos.: 1, 2 and 16.

5. The double-stranded nucleic acid molecule according to claim 4, wherein the sense strand has a nucleotide sequence which corresponds to a target sequence indicated by any one of SEQ ID Nos.: 2 and 16.

6. The double-stranded nucleic acid molecule according to claim 1, wherein the double-stranded nucleic acid molecule is at least one of a double-stranded RNA and a double-stranded RNA-DNA chimera.

7. The double-stranded nucleic acid molecule according to claim 6, wherein the double-stranded nucleic acid molecule is at least one of siRNA and chimera siRNA.

8. DNA comprising:
   a nucleotide sequence encoding a double-stranded nucleic acid molecule which comprises
   (a) a sense strand which comprises a nucleotide sequence corresponding to a target sequence indicated by any one of SEQ ID Nos.: 1 to 38, and
   (b) an antisense strand which comprises a nucleotide sequence complementary to that of the sense strand specified in (a),
   wherein the double-stranded nucleic acid molecule is for suppressing the expression of at least one of COX7RP and estrogen-responsive finger protein (Efp) genes.

9. A vector comprising:
   DNA which comprises a nucleotide sequence encoding a double-stranded nucleic acid molecule which comprises
   (a) a sense strand which comprises a nucleotide sequence corresponding to a target sequence indicated by any one of SEQ ID Nos.: 1 to 38, and
   (b) an antisense strand which comprises a nucleotide sequence complementary to that of the sense strand specified in (a),
   wherein the double-stranded nucleic acid molecule is for suppressing the expression of at least one of COX7RP and estrogen-responsive finger protein (Efp) genes.

10. A cancer cell proliferation inhibitor comprising:
    at least one of a double-stranded nucleic acid molecule which comprises
    (a) a sense strand which comprises a nucleotide sequence corresponding to a target sequence indicated by any one of SEQ ID Nos.: 1 to 38, and
    (b) an antisense strand which comprises a nucleotide sequence complementary to that of the sense strand specified in (a),
    wherein the double-stranded nucleic acid molecule is for suppressing the expression of at least one of COX7RP and estrogen-responsive finger protein (Efp) genes; DNA which comprises a nucleotide sequence encoding the double-stranded nucleic acid molecule; and a vector which comprises the DNA,
    wherein the cancer cell proliferation inhibitor is for inhibiting the growth of at least one of uterine cancer cells, breast cancer cells and bladder cancer cells.

11. A pharmaceutical agent comprising:
    a cancer cell proliferation inhibitor which comprises at least one of a double-stranded nucleic acid molecule which comprises
    (a) a sense strand which comprises a nucleotide sequence corresponding to a target sequence indicated by any one of SEQ ID Nos.: 1 to 38, and
    (b) an antisense strand which comprises a nucleotide sequence complementary to that of the sense strand specified in (a),
    wherein the double-stranded nucleic acid molecule is for suppressing the expression of at least one of COX7RP and estrogen-responsive finger protein (Efp) genes; DNA which comprises a nucleotide sequence encoding the double-stranded nucleic acid molecule; and a vector which comprises the DNA,
    wherein the cancer cell proliferation inhibitor is for inhibiting the growth of at least one of uterine cancer cells, breast cancer cells and bladder cancer cells, and
    wherein the pharmaceutical agent is for treating at least one of uterine cancer, breast cancer and bladder cancer.

* * * * *

SEQUENCE LISTING

```
<160> NUMBER OF SEQ ID NOS: 46

<210> SEQ ID NO 1
<211> LENGTH: 21
<212> TYPE: DNA
<213> ORGANISM: Homo sapiens

<400> SEQUENCE: 1
ctccgattcc acagtgtatg a                                              21

<210> SEQ ID NO 2
<211> LENGTH: 21
<212> TYPE: DNA
<213> ORGANISM: Homo sapiens

<400> SEQUENCE: 2
gtgggaggga ccatctactg c                                              21

<210> SEQ ID NO 3
<211> LENGTH: 21
<212> TYPE: DNA
<213> ORGANISM: Homo sapiens

<400> SEQUENCE: 3
gctgaacaca ggcttgttaa t                                              21

<210> SEQ ID NO 4
<211> LENGTH: 21
<212> TYPE: DNA
<213> ORGANISM: Homo sapiens

<400> SEQUENCE: 4
gtggcttcac gcagaagttg g                                              21

<210> SEQ ID NO 5
<211> LENGTH: 21
<212> TYPE: DNA
<213> ORGANISM: Homo sapiens

<400> SEQUENCE: 5
ctgacctccg attccacagt g                                              21

<210> SEQ ID NO 6
<211> LENGTH: 21
<212> TYPE: DNA
<213> ORGANISM: Homo sapiens

<400> SEQUENCE: 6
catctcctat ctttagtgaa a                                              21
```

```
<210> SEQ ID NO 7
<211> LENGTH: 21
<212> TYPE: DNA
<213> ORGANISM: Homo sapiens

<400> SEQUENCE: 7
gagctcattc gacagttaaa g                                              21

<210> SEQ ID NO 8
<211> LENGTH: 21
<212> TYPE: DNA
<213> ORGANISM: Homo sapiens

<400> SEQUENCE: 8
cttggatggc ttaacatttt t                                              21

<210> SEQ ID NO 9
<211> LENGTH: 21
<212> TYPE: DNA
<213> ORGANISM: Homo sapiens

<400> SEQUENCE: 9
ccgattccac agtgtatgat t                                              21

<210> SEQ ID NO 10
<211> LENGTH: 21
<212> TYPE: DNA
<213> ORGANISM: Homo sapiens

<400> SEQUENCE: 10
gagaatacct gtttagtgtt g                                              21

<210> SEQ ID NO 11
<211> LENGTH: 21
<212> TYPE: DNA
<213> ORGANISM: Homo sapiens

<400> SEQUENCE: 11
gtagcctgcc tctatttgtt g                                              21

<210> SEQ ID NO 12
<211> LENGTH: 21
<212> TYPE: DNA
<213> ORGANISM: Homo sapiens

<400> SEQUENCE: 12
gtgaaatctt atgtgtaatt a                                              21

<210> SEQ ID NO 13
<211> LENGTH: 21
<212> TYPE: DNA
<213> ORGANISM: Homo sapiens

<400> SEQUENCE: 13
cgattccaca gtgtatgatt a                                              21

<210> SEQ ID NO 14
<211> LENGTH: 21
<212> TYPE: DNA
<213> ORGANISM: Homo sapiens

<400> SEQUENCE: 14
gtgtttgtgc tcctgatttc c                                              21
```

```
<210> SEQ ID NO 15
<211> LENGTH: 21
<212> TYPE: DNA
<213> ORGANISM: Homo sapiens

<400> SEQUENCE: 15
caccgtggga acagagaata c                                              21

<210> SEQ ID NO 16
<211> LENGTH: 21
<212> TYPE: DNA
<213> ORGANISM: Homo sapiens

<400> SEQUENCE: 16
gggtgggcgt gcttctcaac t                                              21

<210> SEQ ID NO 17
<211> LENGTH: 21
<212> TYPE: DNA
<213> ORGANISM: Homo sapiens

<400> SEQUENCE: 17
gtccacctga tgtataagtt c                                              21

<210> SEQ ID NO 18
<211> LENGTH: 21
<212> TYPE: DNA
<213> ORGANISM: Homo sapiens

<400> SEQUENCE: 18
gggatgagtt cgagtttctg g                                              21

<210> SEQ ID NO 19
<211> LENGTH: 21
<212> TYPE: DNA
<213> ORGANISM: Homo sapiens

<400> SEQUENCE: 19
cggtgtcatc tcctaacaag g                                              21

<210> SEQ ID NO 20
<211> LENGTH: 21
<212> TYPE: DNA
<213> ORGANISM: Homo sapiens

<400> SEQUENCE: 20
gcccgattcc tcttagagaa a                                              21

<210> SEQ ID NO 21
<211> LENGTH: 19
<212> TYPE: DNA
<213> ORGANISM: Homo sapiens

<400> SEQUENCE: 21
gaccgcagct gcacaagaa                                                 19

<210> SEQ ID NO 22
<211> LENGTH: 21
<212> TYPE: DNA
<213> ORGANISM: Homo sapiens

<400> SEQUENCE: 22
gctatttgtt cgtcatactg t                                              21
```

-continued

```
<210> SEQ ID NO 23
<211> LENGTH: 21
<212> TYPE: DNA
<213> ORGANISM: Homo sapiens

<400> SEQUENCE: 23
ctcgggagag caataatctt t                                              21

<210> SEQ ID NO 24
<211> LENGTH: 21
<212> TYPE: DNA
<213> ORGANISM: Homo sapiens

<400> SEQUENCE: 24
cgggagagca ataatctttg t                                              21

<210> SEQ ID NO 25
<211> LENGTH: 21
<212> TYPE: DNA
<213> ORGANISM: Homo sapiens

<400> SEQUENCE: 25
ctcccaaggg ttgagatttc t                                              21

<210> SEQ ID NO 26
<211> LENGTH: 21
<212> TYPE: DNA
<213> ORGANISM: Homo sapiens

<400> SEQUENCE: 26
gtggtagctg attattcctg t                                              21

<210> SEQ ID NO 27
<211> LENGTH: 21
<212> TYPE: DNA
<213> ORGANISM: Homo sapiens

<400> SEQUENCE: 27
cagtccgtgt ggcatgataa a                                              21

<210> SEQ ID NO 28
<211> LENGTH: 21
<212> TYPE: DNA
<213> ORGANISM: Homo sapiens

<400> SEQUENCE: 28
cctctcacta ttgattttaa t                                              21

<210> SEQ ID NO 29
<211> LENGTH: 21
<212> TYPE: DNA
<213> ORGANISM: Homo sapiens

<400> SEQUENCE: 29
ctgggaagta tcggaaattc c                                              21

<210> SEQ ID NO 30
<211> LENGTH: 21
<212> TYPE: DNA
<213> ORGANISM: Homo sapiens

<400> SEQUENCE: 30
gctccttata gcctaatgtt g                                              21
```

```
<210> SEQ ID NO 31
<211> LENGTH: 21
<212> TYPE: DNA
<213> ORGANISM: Homo sapiens

<400> SEQUENCE: 31
gggatgagtt cgagtttctg g                                              21

<210> SEQ ID NO 32
<211> LENGTH: 21
<212> TYPE: DNA
<213> ORGANISM: Homo sapiens

<400> SEQUENCE: 32
gttcctcggg agagcaataa t                                              21

<210> SEQ ID NO 33
<211> LENGTH: 21
<212> TYPE: DNA
<213> ORGANISM: Homo sapiens

<400> SEQUENCE: 33
gctcccaagg gttgagattt c                                              21

<210> SEQ ID NO 34
<211> LENGTH: 21
<212> TYPE: DNA
<213> ORGANISM: Homo sapiens

<400> SEQUENCE: 34
gacgtgcctt agaaggtttg a                                              21

<210> SEQ ID NO 35
<211> LENGTH: 21
<212> TYPE: DNA
<213> ORGANISM: Homo sapiens

<400> SEQUENCE: 35
cgggtacaaa atgctatttg t                                              21

<210> SEQ ID NO 36
<211> LENGTH: 21
<212> TYPE: DNA
<213> ORGANISM: Homo sapiens

<400> SEQUENCE: 36
gggaacactc tgatacactg g                                              21

<210> SEQ ID NO 37
<211> LENGTH: 21
<212> TYPE: DNA
<213> ORGANISM: Homo sapiens

<400> SEQUENCE: 37
gaggaacctt tgtatccatc t                                              21

<210> SEQ ID NO 38
<211> LENGTH: 21
<212> TYPE: DNA
<213> ORGANISM: Homo sapiens

<400> SEQUENCE: 38
ccccagaggt tcacatactg c                                              21
```

-continued

```
<210> SEQ ID NO 39
<211> LENGTH: 19
<212> TYPE: DNA
<213> ORGANISM: Photinus pyralis

<400> SEQUENCE: 39
cgtacgcgga atacttcga                                                      19

<210> SEQ ID NO 40
<211> LENGTH: 21
<212> TYPE: RNA
<213> ORGANISM: Artificial Sequence
<220> FEATURE:
<223> OTHER INFORMATION: Synthetic

<400> SEQUENCE: 40
guaccgcacg ucauucguau c                                                   21

<210> SEQ ID NO 41
<211> LENGTH: 1145
<212> TYPE: DNA
<213> ORGANISM: Homo sapiens

<400> SEQUENCE: 41
cttctctggg gcggtcgcgt tggcagcgga tgcgggaagc cggactctgg gcgtcatgta         60
ctacaagttt agtggcttca cgcagaagtt ggcaggagca tgggcttcgg aggcctatag        120
cccgcaggga ttaaagcctg tggtttccac agaagcacca cctatcatat tgccacacc         180 aactaaactg acctccgatt ccacagtgta tgattatgct gggaaaaaca agttccaga         240 gctacaaaag tttttccaga aagctgatgg tgtgcccgtc tacctgaaac gaggcctgcc        300
tgaccaaatg ctttaccgga ccaccatggc gctgactgtg gagggacca tctactgcct         360 gatcgccctc tacatggctt cgcagcccaa aaacaaatga gttaggctgc agaggactgg        420
tttgtttttt ggcataaacc ctttgaagtt ccttttttcat tgttaaatta aaattttttt       480
ttttacttgg atggcttaac attttttgcaa gaaaaatagg aagatatgaa gatgatgttt       540
tggtttgttt atgaaatgca tatggcttgt cagagctcat tcgacagtta aagccattgt        600
ttaaagaaat ggtgctttgc tctgtgtttg tgctcctgat ttccctggag gttctggatg        660
aaggctgaac acaggcttgt taatgtcagt ctgtgctgag gacctcaggg acttgaggtt        720
gcatttttga gcatggggtg caggagcctt tctggatttg gatgtggcta tggaaagaac        780
acagaagcca aggtcatgtg catgaaatga ggagtttgag ttagtcacct cggggattt         840 ttccattttg cagtaaaatg ttaaattaat gtagcctgcc tctatttgtt gggcaggtaa        900
tttcaagggg ttatttgcct catctccat ctttagtgaa atcttatgtg taattattcc         960
accgtgggaa cagagaatac ctgtttagtg ttgcacttta gactggtgtc tgttttgtta       1020
atgcagctgt gccacaaatt ctcctttatc ttttaaaaat gttatagctt taaattttga       1080 tttatttga ctgtggaata aatacatgaa tgaaaaaaaaa aaaaaaaaaa aaaaaaaaaa       1140
aaaaa                                                                  1145

<210> SEQ ID NO 42
<211> LENGTH: 5744
<212> TYPE: DNA
<213> ORGANISM: Homo sapiens

<400> SEQUENCE: 42
gtttcctcgg cggcctcgga gcgcgggtgc agcagttgtg tcccgacccc tgggagcgcc         60
atggcagagc tgtgccccct ggccgaggag ctgtcgtgct ccatctgcct ggagcccttc        120
```

```
aaggagccgg tcaccactcc gtgcggccac aacttctgcg ggtcgtgcct gaatgagacg      180
tgggcagtcc agggctcgcc atacctgtgc ccgcagtgcc gcgccgtcta ccaggcgcga      240
ccgcagctgc acaagaacac ggtgctgtgc aacgtggtgg agcagttcct gcaggccgac      300
ctggcccggg agccacccgc cgacgtctgg acgccgcccg cccgcgcctc tgcacccagc      360
ccgaatgccc aggtggcctg cgaccactgc ctgaaggagg ccgccgtgaa gacgtgcttg      420
gtgtgcatgg cctccttctg tcaggagcac ctgcagccgc acttcgacag ccccgccttc      480
caggaccacc cgctgcagcc gcccgttcgc gacctgttgc gccgcaaatg ttcccagcac      540
aatcggctgc gggaattttt ctgccccgag cacagcgagt gcatctgcca catctgcctg      600
gtggagcata agacctgctc tcccgcgtcc ctgagccagg ccagcgccga cctggaggcc      660
accctgaggc acaaactaac tgtcatgtac agtcagatca acgggcgtc gagagcactg       720 gatgatgtga gaaacaggca gcaggatgtg cggatgactg caaacagaaa ggtggagcag      780
ctacaacaag aatacgcgga aatgaaggct ctcttggacg cctcagagac cacctcgaca      840
aggaagataa aggaagagga gaagagggtc aacagcaagt tgacaccat ttatcagatt       900 ctcctcaaga gaagagtga gatccagacc ttgaaggagg agattgaaca gagcctgacc       960
aagagggatg agttcgagtt tctggagaaa gcatcaaaac tgcgaggaat ctcaacaaag     1020
ccagtctaca tccccgaggt ggaactgaac acaagctga taaaaggcat ccaccagagc      1080
accatagacc tcaaaaacga gctgaagcag tgcatcgggc ggctccagga gcccacccccc     1140 agttcaggtg accctggaga gcatgaccca gcgtccacac acaaatccac acgccctgtg     1200
aagaaggtct ccaaagagga aaagaaatcc aagaaacctc cccctgtccc tgccttaccc     1260
agcaagcttc ccacgtttgg agccccggaa cagttagtgg attaaaaaca agctggcttg     1320
gaggctgcag ccaaagccac cagctcacat ccgaactcaa catctctcaa ggccaaggtg     1380
ctggagacct tcctggccaa gtccagacct gagctcctgg agtattacat taaagtcatc     1440
ctggactaca acaccgccca caacaaagtg gctctgtcag agtgctatac agtagcttct     1500
gtggctgaga tgcctcagaa ctaccggccg catccccaga ggttcacata ctgctctcag     1560
gtgctgggcc tgcactgcta caagaagggg atccactact gggaggtgga gctgcagaag     1620
aacaacttct gtggggtagg catctgctac ggaagcatga accggcaggg cccagaaagc     1680
aggctcggcc gcaacagcgc ctcctggtgc gtggagtggt caacaccaa gatctctgcc      1740 tggcacaata acgtggagaa aaccctgccc tccaccaagg ccacgcgggt gggcgtgctt     1800
ctcaactgtg accacggctt tgtcatcttc ttcgctgttg ccgacaaggt ccacctgatg     1860
tataagttca gggtggactt tactgaggct ttgtacccgg cttttctgggt atttttctgct     1920 ggtgccacac tctccatctg ctcccccaag taggcaggct gtaggcactt gggctgactg     1980
cctgcagaag tcccaagacc ctagtgaaaa tacagcaggc agaactctcc ttggataatt     2040
ccccaagagg tcccaaggat tgggagcatg ggaggggagc tggcgggagg gtgggaggtg     2100
ggatttagcc aggaaagggg tgagagtgat tgtgttgtgg gcgaggaggc gtttccaccc     2160
cctggtgcct atcagggcag ggtgacctac tccccattgt tctggaaatc tccaggctgc     2220
tgggcagctg ggcagagctc tgggaagtga agtcatgagt gcccgattcc tcttagagaa     2280
aatccatagc tactgtaggt tctgtcttgg gccacttgga tctgaaggct gccccttttgc     2340 tctctggggt agccttcaga tcttggtgtt ttgaattctt actatagatg tttttaaagt      2400
tccaaagtca ttgagtttca atgttacata aactccatta cccgcatgtt ggggcttgat     2460
ctcctggtta ttatctgtgc ttgaggaaac acccacagca gtctctaccc agaacagttt      2520
```

```
cctaaagagg catacccuct tcctccactg gaaaatagtg cgttcccuc ctaccctgca   2580 cacccatcgc ccccacattg atggtttca aacagcaaac ttttcagcta aagcttcaaa   2640
ccatgattgg aatcagcctg tgttggattt gtgattcagg gtcatggtga ccctgatcca   2700
gtttgggtgg aaatccttcc taagtatcat aagaagcatc ttggcagaga tgctttggtg   2760
gcagccatga gctttgctgg aggccttgct tcccatagcc ttggctgtgg ggcaaggaac   2820
tctgccaggc gagggggatg ctgccctgga tcaacagaag cctggtgggt ttgctcgtgt   2880
tagagtgtcc tgccttctta ctgacaactc ttctcggtga tagcctctct tccctggatt   2940
gtgacatatg aatgacagt gcaggtacca ccgaggctag cacagtcaag cctccagcta   3000
agctggatcc ctgaagcctg ctatcatgca gacaggctat gcggctgcct cggaccatgc   3060
taggccactt gctgggtgt caacctacca ccaaaggggt cttttagcaa acctcatggg   3120
gaacaggaac attcctgttc atccctggcc acaggctgca gacccagcac tggcccttgc   3180
gtgagtcaga gcctggggct ggccctagcc ccttctactg acttcctcat ttaagccaat   3240
tatataagct cacattgatc agggagggag ggaaagagct aaagagggtc acacaagtgg   3300
ctattttccc tgcagtgttt ctgtgtggtg aaaataaccc agtccactaa ggggcgggag   3360
tgaatggatg gctggatttt ccccaagctc cttatagcct aatgttgtca ggatgtgagt   3420
atgaggaatt tagcctctta tagtgaaatg agtccaactc tgggctttgc ttagaggaga   3480
gctcctgtca ggcttcctat aatatgaaaa gaagtcacca ttggggaact agagaccca   3540 gacctttca tatggatatt tgagaatgta atgcatctca ggcctcgtgc tggaactcta   3600
gggcactcta ggcaggctca gaacacttga tattcctgac agctacacac ctgacatgca   3660
ggtacatacc tgatcggtgt catctcctaa caaggatttt cagttcctcg ggagagcaat   3720
aatctttgta ggaaagacat ccctgcaata ggtgatatgt ggtccttaga agttttattc   3780
ctttactact tggaagaaaa gttctttggt gattcttctc tgcttttgaa gatgatcaaa   3840
agcatcttca ttgatttct gaaacgaaag ccttgtctga aaccaattaa tacttgggaa   3900
acagctgggc ttggaggagt agaatgccag agataaatcc atggctcctg ctctggctct   3960
cttctgcaga aatgagggca acagtgaggc cacttccctg gcaaatgtgc agctcaggat   4020
agggaagcat aagaccctct gtttaaaaga gagtcaagta ggtaaccaaa gccaagctct   4080
gtgcaaggtg ctttggagtt gtaaattgag gagtgcatcc ttgctgtctt gaaccattct   4140
gtttgcaatg gtgagacctt acataaccta gccttgcagg gccgccacac aaccctggag   4200
tcctagagtt ggaggaacct ttgtatccat ctgacttctc attttgcaga atatgatgag   4260
aaagtagagg atcgctctgt tcaccactct tgctattcca ttagtgggga gatgcctgct   4320
agcatgtgtg agggaacac tctgatacac tgggaagtat cggaaattcc cagaaacaca   4380
aacataaaat aactctccta gacccaggta ctggggactg tctcagtccg tgtggcatga   4440
taaataaaag gttaggatca agtctttgta ttttcaaga tgtggtagct gattattcct   4500
gttttaagta ctctgaaatt gatctgtgat caataatact aatatgttat cttttaccgt   4560
attctgcctc tcactattga ttttaattag ttaggagtat ttgagctgtt atttcttgag   4620
cttaatattt ttttagagtt aactcttaa ggagataatc atggctgtag acaaggccag   4680
ggctggctga cgtgccttag aaggtttgaa tgcaataaag cggtgtttgg cgttctcctg   4740
cattgtagtg cgggtacaaa atgctatttg ttcgtcatac tgttgtcagc agatgagccg   4800
cccactacag acggctactg cccagggacc tgcccaggcc ccacccaagg gctcccaagg   4860
gttgagattt ctgcagacct atagccagca cacttagtcc tgccctatat agagttcctc   4920
```

```
ttcgggaagc ttttgataag gaattctcag accgatagga tgtctgtctg ggctttgctg    4980
cgggacagtc taactgtggg ggctagggga aagcaggaga gtatcgatca aagagtaagc    5040
cacacacgga taatcagtta ctagggatgg aggtgtgagg gttcattata ttattcattt    5100
tactgttgta tatgtttgaa aatgtctata ataaaaagct ttaaaaaaaa aaagaaaca     5160 aaaatagttc aggccagcaa tgggccctcc atgttcagtg gattttatcc ttgtttcaat    5220
tggggtagga gttccaggag gtgtggattg gaggttgtct aaagaattga actggccttt    5280
gtccctgctt cctgggaggg agactttcag tccttgacat ttccagggta ataggagtgt    5340
ctttgttatt tgtgaggcca tgggatcaca cctgagctta tgctaaaagg tgggatgact    5400
cagagctggg gctggtcacc agacagactg accatgtgat tagaggtttg aggctttgag    5460
tcagcctgac ctatggggcg ggggactgga ggctgagttt aatcatctgg ccagtgcttt    5520
aatcagtaca tcatgaaacc ctaataaaaa ctctggacac taaagctcag catagcttcc    5580
tgggtggtga agctgtggct atgccggcag ggcagtgtgc cctaattcca cgaagagggg    5640
gcatgggagc actgtgctca agacccttcc agacctttcc ctgtgtcttc cttggcttgt    5700
ggagctgatt tgtatccttt ataataaaac taatcataag tata                    5744
```

<210> SEQ ID NO 43
<211> LENGTH: 21
<212> TYPE: DNA
<213> ORGANISM: Artificial Sequence
<220> FEATURE:
<223> OTHER INFORMATION: Synthetic

<400> SEQUENCE: 43
gugggaggga ccatctactg c    21

<210> SEQ ID NO 44
<211> LENGTH: 21
<212> TYPE: DNA
<213> ORGANISM: Artificial Sequence
<220> FEATURE:
<223> OTHER INFORMATION: Synthetic

<400> SEQUENCE: 44
gugggaggga ccatctactg c    21

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45
cttgugggag ggacacatcg c    21

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46 ctagggtuggg cguucgtacc t    21